United States Patent
Allen et al.

(10) Patent No.: US 9,414,903 B2
(45) Date of Patent: Aug. 16, 2016

(54) PELVIC IMPLANT SYSTEM AND METHOD

(75) Inventors: John J. Allen, Mendota Heights, MN (US); James R. Mujwid, Crystal, MN (US); Kevin R. Arnal, Excelsior, MN (US); Jessica E. Felton, Minneapolis, MN (US); Robert E. Lund, St. Michael, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 0 days.

(21) Appl. No.: 13/556,167

(22) Filed: Jul. 23, 2012

(65) Prior Publication Data

US 2013/0023724 A1 Jan. 24, 2013

Related U.S. Application Data

(60) Provisional application No. 61/510,726, filed on Jul. 22, 2011, provisional application No. 61/515,180, filed on Aug. 4, 2011, provisional application No. 61/545,104, filed on Oct. 7, 2011, provisional (Continued)

(51) Int. Cl.
*A61F 2/00* (2006.01)
*A61F 2/02* (2006.01)
(Continued)

(52) U.S. Cl.
CPC ........... *A61F 2/0045* (2013.01); *A61B 17/0401* (2013.01); *A61F 2/0036* (2013.01); *A61B 2017/00805* (2013.01); *A61B 2017/00867* (2013.01); *A61B 2017/0409* (2013.01); *A61B 2017/0412* (2013.01); *A61B 2017/0417* (2013.01); *A61B 2017/0496* (2013.01);

(Continued)

(58) Field of Classification Search
CPC . A61F 2/0036; A61F 2/0045; A61B 17/0401; A61B 2017/00805; A61B 2017/00867; A61B 2017/06176; A61B 2017/0412; A61B 2017/0417; A61B 2017/0496; A61B 2017/06052; A61B 2017/0409
USPC ..................................................... 600/29, 30
See application file for complete search history.

(56) References Cited

U.S. PATENT DOCUMENTS 2,738,790 A 3/1956 Todt et al.
3,124,136 A 3/1964 Usher (Continued)

FOREIGN PATENT DOCUMENTS

AU 2002241673 11/2005
CA 2404459 8/2005

(Continued)

OTHER PUBLICATIONS

"Access Instrument System with AlloSling Fascia" (5 pages with two pages of Instructions for Use).

(Continued)

*Primary Examiner* — Navin Natnithithadha
*Assistant Examiner* — Sunita Reddy
(74) *Attorney, Agent, or Firm* — Skaar Ulbrich Macari, P.A.

(57) ABSTRACT

Systems and methods are provided and adapted to engage and pull (e.g., pull up) or reposition paraurethral support tissue, such as the perineal membrane. The perineal membrane intersects the urethra and vagina at the midurethra or distal location and can thus be stabilized or controlled in a manner that helps restore continence. As such, the implants can be utilized to eliminate the need for mesh or other supportive structures under the urethra that is common with other incontinence slings.

36 Claims, 27 Drawing Sheets

Related U.S. Application Data application No. 61/547,467, filed on Oct. 14, 2011, provisional application No. 61/547,503, filed on Oct. 14, 2011, provisional application No. 61/607,332, filed on Mar. 6, 2012, provisional application No. 61/607,891, filed on Mar. 7, 2012, provisional application No. 61/608,436, filed on Mar. 8, 2012, provisional application No. 61/608,478, filed on Mar. 8, 2012, provisional application No. 61/653,199, filed on May 30, 2012, provisional application No. 61/653,213, filed on May 30, 2012, provisional application No. 61/653,224, filed on May 30, 2012, provisional application No. 61/653,236, filed on May 30, 2012.

(51) Int. Cl.
  *A61B 17/04* (2006.01)
  *A61B 17/00* (2006.01)
  *A61B 17/06* (2006.01)

(52) U.S. Cl.
  CPC ............... *A61B2017/06052* (2013.01); *A61B 2017/06176* (2013.01)

(56) References Cited

U.S. PATENT DOCUMENTS

| | | |
|---|---|---|
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Velaquez |
| 5,474,543 A | 12/1995 | McKay |
| 5,518,504 A | 5/1996 | Polyak |
| 5,520,606 A * | 5/1996 | Schoolman et al. ............ 600/31 |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,993,459 A | 11/1999 | Larsen et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |

(56) References Cited

U.S. PATENT DOCUMENTS

| | | |
|---|---|---|
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosely et al. |
| 7,789,821 B2 | 9/2010 | Browning |
| 7,981,024 B2 | 7/2011 | Levy |
| 8,172,745 B2 | 5/2012 | Rosenblatt |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0143234 A1* | 10/2002 | LoVuolo ......................... 600/30 |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0161382 A1 | 10/2002 | Neisz et al. |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0039453 A1 | 2/2004 | Anderson et al. |
| 2004/0073235 A1 | 4/2004 | Lund |
| 2004/0106847 A1 | 6/2004 | Benderev |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0033363 A1 | 2/2005 | Bojarski et al. |
| 2005/0038451 A1 | 2/2005 | Rao et al. |

(56) References Cited

U.S. PATENT DOCUMENTS

| | | | |
|---|---|---|---|
| 2005/0055104 A1 | 3/2005 | Arnal et al. | |
| 2005/0131391 A1 | 6/2005 | Chu et al. | |
| 2005/0131393 A1 | 6/2005 | Chu et al. | |
| 2005/0199249 A1 | 9/2005 | Karram | |
| 2005/0245787 A1 | 11/2005 | Cox et al. | |
| 2005/0256530 A1 | 11/2005 | Petros | |
| 2005/0277806 A1 | 12/2005 | Cristalli | |
| 2005/0278037 A1 | 12/2005 | Delorme et al. | |
| 2005/0283189 A1 | 12/2005 | Rosenblatt et al. | |
| 2006/0015010 A1 | 1/2006 | Jaffe et al. | |
| 2006/0028828 A1 | 2/2006 | Cox et al. | |
| 2006/0058578 A1 | 3/2006 | Browning | |
| 2006/0089524 A1 | 4/2006 | Chu | |
| 2006/0089525 A1* | 4/2006 | Mamo et al. | 600/37 |
| 2006/0122457 A1 | 6/2006 | Kovac | |
| 2006/0173237 A1 | 8/2006 | Jacquetin | |
| 2006/0195007 A1 | 8/2006 | Anderson | |
| 2006/0195010 A1* | 8/2006 | Arnal et al. | 600/30 |
| 2006/0195011 A1 | 8/2006 | Arnal | |
| 2006/0205995 A1 | 9/2006 | Browning | |
| 2006/0217589 A1 | 9/2006 | Wan et al. | |
| 2006/0229493 A1 | 10/2006 | Weiser et al. | |
| 2006/0229596 A1 | 10/2006 | Weiser et al. | |
| 2006/0252980 A1 | 11/2006 | Arnal et al. | |
| 2006/0287571 A1 | 12/2006 | Gozzi | |
| 2007/0015953 A1 | 1/2007 | MacLean | |
| 2007/0078295 A1 | 4/2007 | Iandgrebe | |
| 2007/0173864 A1* | 7/2007 | Chu | 606/139 |
| 2008/0039678 A1 | 2/2008 | Montpetit et al. | |
| 2008/0045782 A1 | 2/2008 | Jimenez et al. | |
| 2008/0057261 A1 | 3/2008 | Rock et al. | |
| 2008/0140218 A1 | 6/2008 | Staskin et al. | |
| 2008/0207988 A1 | 8/2008 | Hanes | |
| 2008/0300607 A1 | 12/2008 | Meade et al. | |
| 2009/0005634 A1 | 1/2009 | Rane | |
| 2009/0012353 A1 | 1/2009 | Beyer | |
| 2009/0182190 A1 | 7/2009 | Dann | |
| 2009/0221868 A1 | 9/2009 | Evans | |
| 2009/0222025 A1* | 9/2009 | Catanese et al. | 606/139 |
| 2010/0010631 A1 | 1/2010 | Otte et al. | |
| 2010/0022822 A1 | 1/2010 | Walshe | |
| 2010/0105979 A1 | 4/2010 | Hamel et al. | |
| 2010/0174134 A1 | 7/2010 | Anderson et al. | |
| 2010/0179575 A1 | 7/2010 | Von Pechmann et al. | |
| 2010/0197999 A1* | 8/2010 | Deegan et al. | 600/30 |
| 2010/0210897 A1 | 8/2010 | Arnal et al. | |
| 2010/0256443 A1 | 10/2010 | Griguol | |
| 2010/0261950 A1 | 10/2010 | Lund | |
| 2010/0280627 A1 | 11/2010 | Hanes, II | |
| 2010/0305695 A1 | 12/2010 | Devonec | |
| 2010/0331612 A1* | 12/2010 | Lashinski et al. | 600/37 |
| 2011/0082328 A1* | 4/2011 | Gozzi et al. | 600/30 |
| 2011/0112357 A1 | 5/2011 | Chapman et al. | |
| 2011/0124954 A1 | 5/2011 | Ogdahl | |
| 2011/0144417 A1 | 6/2011 | Jagger et al. | |
| 2011/0174313 A1 | 7/2011 | Von Pechmann et al. | |
| 2011/0201876 A1 | 8/2011 | Roll et al. | |
| 2011/0230707 A1 | 9/2011 | Roll et al. | |
| 2012/0016185 A1 | 1/2012 | Sherts et al. | |
| 2012/0130424 A1 | 5/2012 | Sengun et al. | |
| 2012/0203060 A1 | 8/2012 | Roll et al. | |
| 2012/0303059 A1 | 11/2012 | Saadat et al. | |
| 2013/0023724 A1 | 1/2013 | Allen et al. | |
| 2013/0204075 A1 | 8/2013 | Allen et al. | |
| 2015/0238297 A1 | 8/2015 | Roll et al. | |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO9959477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004/017862 | 3/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |

(56) References Cited

FOREIGN PATENT DOCUMENTS

| WO | WO2005122954 A1 | 12/2005 |
|----|-----------------|---------|
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994   | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | 2008152435 A1 | 12/2008 |
| WO | WO2009005714 A2 | 1/2009 |
| WO | WO2009017680 A2 | 2/2009 |
| WO | WO2011/082350 | 7/2011 |
| WO | 2013016306 A1 | 1/2013 |

OTHER PUBLICATIONS

"Introducing: AlloSling Fascia the *Natural Choice* for Suburethral Sling Procedures", Advertisement from UroMed Corporation (1 page).

"We're staying ahead of the curve" Introducing the IVS Tunneller Device for Tension Free Procedures, Tyco Healthcare, 3 pages (2002).

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

AlloSource product literature (11pages).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology, vol. 144, pp. 319-323 (Aug. 1990).

Asmussen, M. et.al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blaivas, Jerry, Commentary: Pubovaginal Sling Procedure, Experience with Pubovaginal Slings, pp. 93-101 (1990).

Boyles, Sarah Hamilton et al., Procedures for Urinary Incontinence in the United States, 1979-1997, Am J Obstet Gynecol, vol. 189, n. 1, pp. 70-75 (Jul. 2003).

Bryans, Fred E., Marlex Gauze Hammock Sling Operation With Cooper'S Ligament Attachment in the Management of Recurrent Urinary Stress Incontinence, American Journal of Obstetrics and Gynecology, vol. 133, pp. 292-294 (Feb. 1979).

Burch, John C., Urethrovaginal Fixation to Cooper'S Ligament for Correction of Stress Incontinence, Cystocele, and Prolapse, Am. J. Obst. & Gyn, vol. 31, pp. 281-290 (1961).

Capio™ CL—Transvaginal Suture Capturing Device—Transvaginal Suture Fixation to Cooper's Ligament for Sling Procedures, Boston Scientific, Microvasive®, 8 pages, (2002).

Cervigni, Mauro et al., The Use of Synthetics in the Treatment of Pelvic Organ Prolapse, Voiding Dysfunction and Female Urology, vol. 11, pp. 429-435 (2001).

Choe, Jong M. et al., Gore-Tex Patch Sling: 7 Years Later, Urology, vol. 54, pp. 641-646 (1999).

Comparison of Tissue Reaction of Monofilament and Multifilament Polypropylene Mesh—A Case Report, Tyco Healthcare, United States Surgical, 4 pages (no date).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Das, Sakti et al., Laparoscopic Colpo-Suspension, The Journal of Urology, vol. 154, pp. 1119-1121 (Sep. 1995).

Debodinance, Philipp et al., "Tolerance of Synthetic Tissues in Touch With Vaginal Scars: Review to the Point of 287 Cases", European Journal of Obstetrics & Gynecology and Reproductive Biology 87 (1999) pp. 23-30.

Decter, Ross M., Use of the Fascial Sling for Neurogenic Incontinence: Lessons Learned, The Journal of Urology, vol. 150, pp. 683-686 (Aug. 1993).

Delancey, John, MD, Structural Support of the Urethra as It Relates to Stress Urinary Incontinence: The Hammock Hypothesis, Am J Obstet Gynecol, vol. 170 No. 6, pp. 1713-1723 (Jun. 1994).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).

Falconer, C. et al., Influence of Different Sling Materials of Connective Tissue Metabolism in Stress Urinary Incontinent Women, International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce With Marlex Mesh for the Treatment of Cystoceles, International Urogynecology Journal, vol. 9, pp. 200-204 (1998).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138 (Sep. 1987).

(56) References Cited

OTHER PUBLICATIONS

Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide, 6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101, n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
Intramesh L.I.F.T. Siliconized polyester, Cousin Biotech, 1 page (no date).
Intramesh® L.I.F.T.® Polypropylene Less Invasive Free Tape, Cousin Biotech, 2 pages (no date).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages (2001).
IVS Tunneller, AMA, (no date) 4 pages.
IVS Tunneller, Australian Medical Design Breakthrough for GSI, mixed incontinence and vault prolapse, AMA Medical Products, 4 pages (no date).
Jeffcoate, T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontintence, British Journal of Obstetrics and Gynaecology, vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).
Korda, A. et al., Experience With Silastic Slings for Female Urinary Incontinence, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kovac, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).
Leach, Gary E., MD, Bone Fixation Technique for Transvaginal Needle Suspension, Urology vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
LigiSure Atlas™, Tyco Healthcare, Valleylab®, 2 pages (no date).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Vote Vaginale Des Prolapsus Genitaux, J Gynecol Obstet Biol Reprod, vol. 28, pp. 825-829 (1999).
Marchionni, Mauro et al., True Incidence of Vaginal Vault Prolapse—Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at the University of Michigan, Journal of Urology, vol. 138, pp. 90-93 (1987).
McGuire, Edwared J. et al., Abdominal Fascial Slings, Slings, Raz Female Urology, p. 369-375 (1996).
McGuire, Edwared J., M.D., The Sling Procedure for Urinary Stress Incontinence, Profiles in Urology, pp. 3-18.
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Mitek Brochure, Therapy of Urinary Stess Incontinence in Women Using Mitek GIII Anchors, by Valenzio C. Mascio, MD.

(56) References Cited

OTHER PUBLICATIONS

Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., A Simplified Sling Operation Suitable for Routine Use, Gynecological and Obstetrical Clinic, University of Vienna, vol. 84, No. 3, p. 400-405, (Aug. 1, 1962).
Natale, F. et al., Tension Free Cystocele Repair (TCR): Long-Term Follow-Up, International Urogynecology Journal, vol. 11, supp. 1, p. S51 (Oct. 2000).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endouroloy, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).
Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetricia et Gynecologica Scandinavica, vol. 69 Sup. 153, pp. 7-31 (1990).

Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pelvic Floor Rehabilitation According to the Integrated Theory of Female Urinary Incontinence, Chapter 7, pp. 249-258 (book chapter).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV— (With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Further Development of the Intravaginal Slingplasty Procedure—IVS V—With "Double Breasted" Unattached Vaginal Flap Repair and Permanent Sling)., Scandinavian Journal of Neurourology and Urodynamics, Sup 153, pp. 77-79 (1993).
Petros, Peter E. Papa et al., The Intravaginal Slingplasty Operation, a Minimally Invasive Technique for Cure of Urinary Incontinence in the Female, Aust. NZ J Obstet Gynaecol, vol. 36, n. 4, pp. 453-461 (1996).

(56) References Cited

OTHER PUBLICATIONS

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, p. 46,48,49 (Jun. 2000).
Raz, Shlomo, et al., The Raz Bladder Neck Suspension Results in 206 Patients, The Journal of Urology, pp. 845-846 (1992).
Raz, Shlomo, Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Readjustable REMEEX® system, Neomedic International, 8 pages (no date).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
SABRE™ Bioabsorbable Sling, Generation Now, Mentor, 4 pages (May 2002).
SABRE™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin et al., A Comparison of Tensile Strength among Three Preparations of Irradiated and Non-Irradiated Human Fascia Lata Allografts (2 pages).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Suport™ , Sub-Urethral Perineal Retro-Pubic Tensionless Sling, Matrix Medical (Pty) Ltd, (no date), 1 pg.
Swift, S.E., et al., Case-Control Study of Etiologic Factors in the Development of Sever Pelvic Organ Prolapse, Int Urogynecol J, vol. 12, pp. 187-192 (2001).
T-Sling® (Totally Tension-free) Urinary Incontinence Procedure, Herniamesh, 2 pages (no date).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).
UroMed Access Instrument System for the Sub-urethral Sling Procedure Catalog No. 120235, Directions for Use, (3 pages).
Vesica® Percutaneous Bladder Neck Stabilization Kit, A New Approach to Bladder Neck Suspenison, Microvasive® Boston Scientific Corporation, 4 pages (1995).
Vesica® Sling Kits, Simplifying Sling Procedures, Microvasive® Boston Scientific Corporation, 4 pages (1998).

(56) References Cited

OTHER PUBLICATIONS

Villet, R., Reponse De R. Villet À L'Article De D. Dargent et al., Gynécolgie Obstétrique & Fertilité, vol. 31, p. 96 (2003).

Visco, Anthony G. et al., Vaginal Mesh Erosion After Abdominal Sacral Colpopexy, Am J Obstet Gynecol, vol. 184, n. 3, pp. 297-302 (297-302).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).

Webster, George D., Female Urinary Incontinence, Urologic Surgery, pp. 665-679.

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology, vol. XX, No. 4, pp. 408-411 (Oct. 1982).

Winters et al., Abdominal Sacral Colpopexy and Abdominal Enterocele Repair in the Management of Vaginal Vault Prolapse, Urology, vol. 56, supp. 6A, pp. 55-63 (2000).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et al., Pulsion Enterocele: Long-Term Results of an Abdominoperineal Technique, Obstetrics & Gynecology, vol. 55 No. 2, pp. 141-148 (Feb. 1980).

Zacharin, Robert, The Suspensory Mechanism of the Female Urethra, Journal of Anatomy, vol. 97, Part 3, pp. 423-427 (1963).

Zimmern, Phillippe E. et al., Four-Corner Bladder Neck Suspension, Vaginal Surgery for the Urologist, vol. 2, No. 1, pp. 29-36 (Apr. 1994).

Le point sur l'incontinence urinaire, Expertise et Practiques en Urologie, No. 3. Dr. Sophie Conquy [Hospital Cochin, Paris]. pp. 17-19.

Mouly, Patrick et al., Vaginal Reconstruction of a Complete Vaginal Prolapse: The Trans Obturator Repair, Journal of Urology, vol. 169, p. 183 (Apr. 2003).

Pourdeyhimi, B, Porosity of Surgical Mesh Fabrics: New Technology, J. Biomed. Mater. Res.: Applied Biomaterials, vol. 23, No. A1, pp. 145-152 (1989).

Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).

Petros, Papa PE et al., An Integral Theory and Its Method for the Diagnosis and Management of Female Urinary Incontinence, Scandinavian Journal of Urology and Nephrology, Supplement 153: p. 1 (1993).

Horbach, Nicollette, Suburethral Sling Procedures, Genuine Stress Incontinence, Chapter 42, pp. 569-579.

Mentor Porges, Uratape, ICS/IUGA Symp, Jul. 2002.

Internal Written Opinion rendered by the International Searching Authority on Sep. 27, 2012 for PCT Application No. PCT/US12/49759, 13 Pages.

International Search Report and Written Opinion rendered by the International Searching Authority on Sep. 17, 2012 for PCT Application No. PCT/US12/47899, 11 Pages.

International Search Report rendered by the International Searching Authority on Sep. 27, 2012 for PCT Application No. PCT/US12/49759, 2 Pages.

* cited by examiner

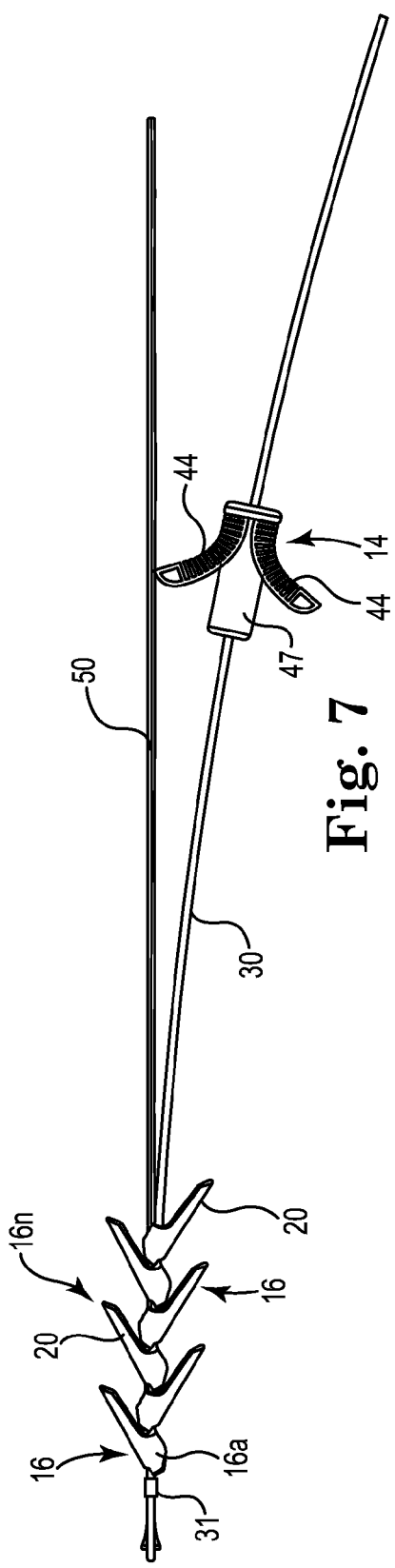
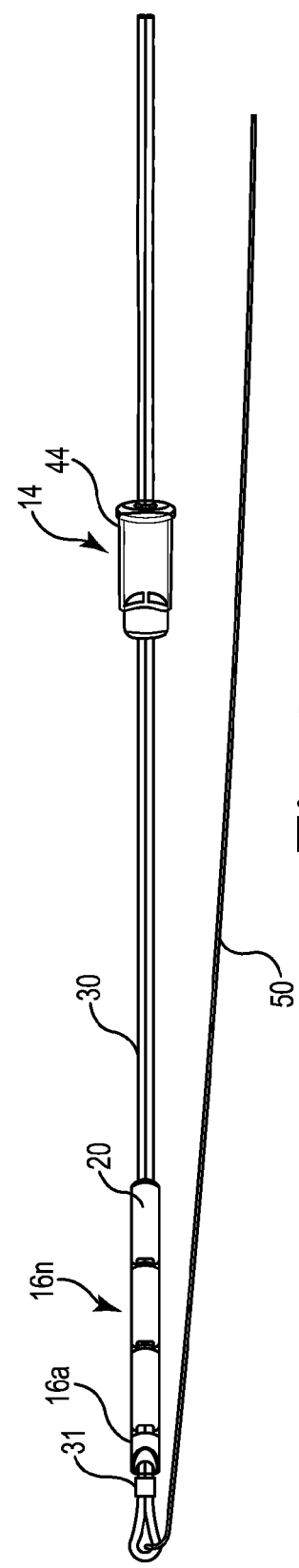

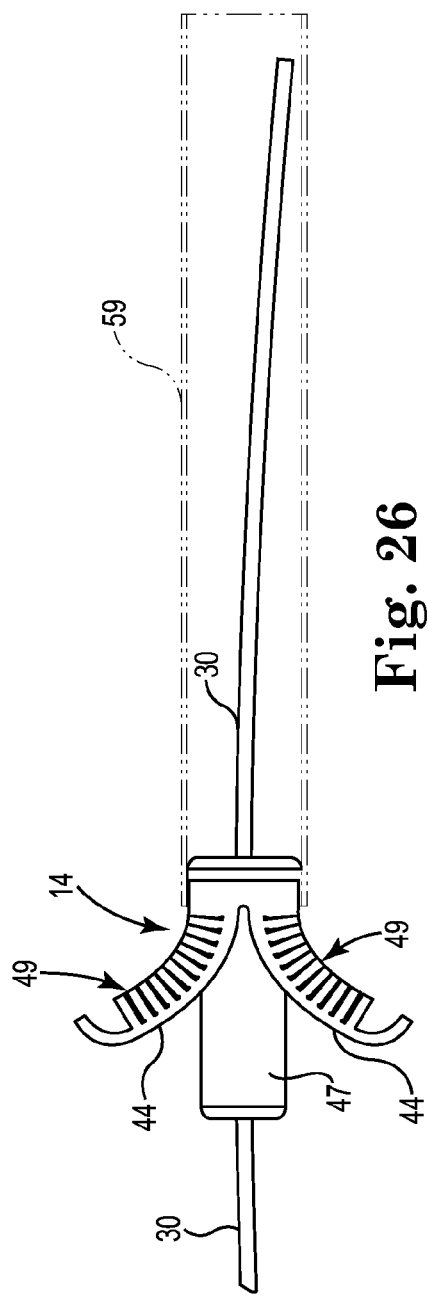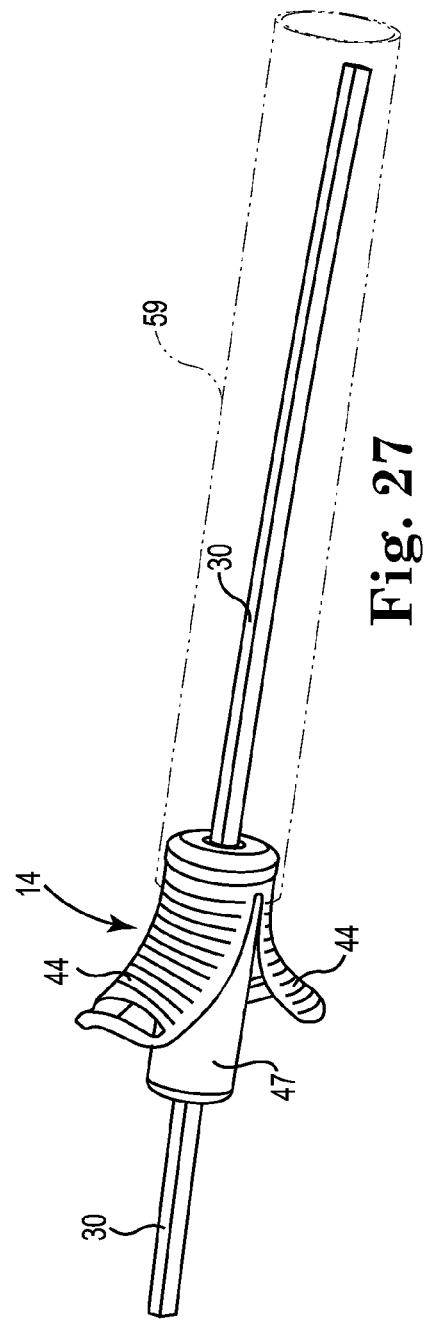

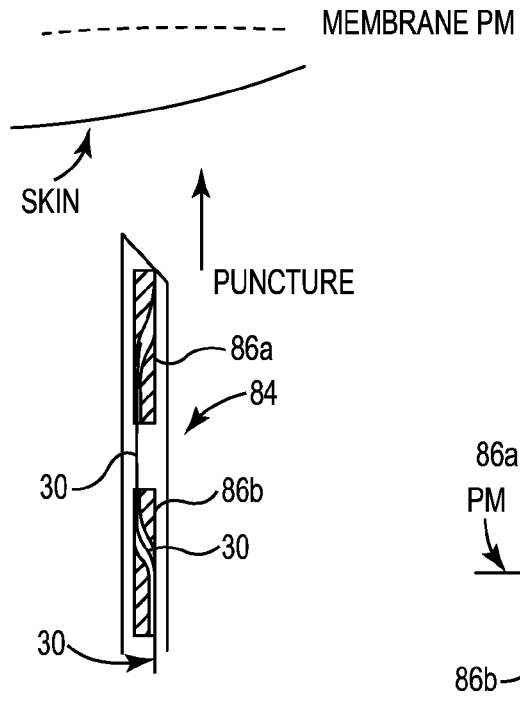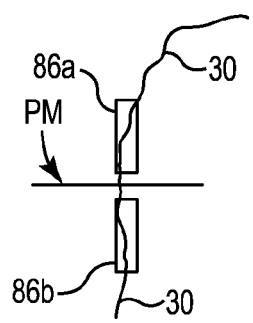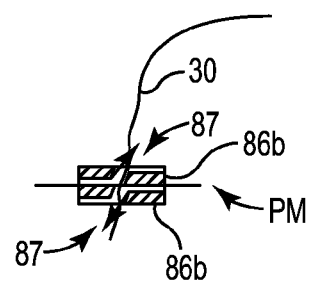
Fig. 43       Fig. 44       Fig. 45
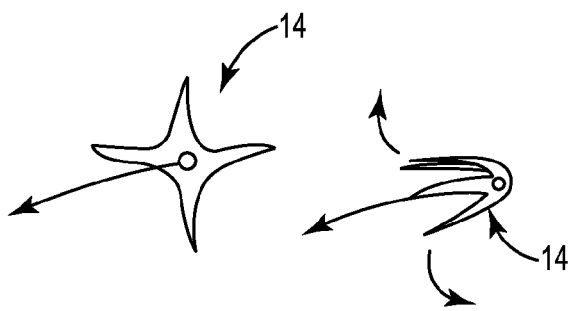
Fig. 46    Fig. 47

PELVIC IMPLANT SYSTEM AND METHOD

PRIORITY

This application claims priority to and the benefit of U.S. Provisional Patent Application No. 61/510,726, filed Jul. 22, 2011, U.S. Provisional Patent Application No. 61/515,180, filed Aug. 4, 2011, U.S. Provisional Patent Application No. 61/545,104, filed Oct. 7, 2011, U.S. Provisional Patent Application No. 61/547,467, filed Oct. 14, 2011, U.S. Provisional Patent Application No. 61/547,503, filed Oct. 14, 2011, U.S. Provisional Patent Application No. 61/607,332, filed Mar. 6, 2012, U.S. Provisional Patent Application No. 61/607,891, filed Mar. 7, 2012, U.S. Provisional Patent Application No. 61/608,436, filed Mar. 8, 2012, U.S. Provisional Patent Application No. 61/608,478, filed Mar. 8, 2012, U.S. Provisional Patent Application No. 61/653,199, filed May 30, 2012, U.S. Provisional Patent Application No. 61/653,213, filed May 30, 2012, U.S. Provisional Patent Application No. 61/653,224, filed May 30, 2012, and U.S. Provisional Patent Application No. 61/653,236, filed May 30, 2012; with each of the above-referenced applications and disclosures incorporated herein by reference in their entirety.

FIELD OF THE INVENTION

The present invention relates to apparatus, tools and methods for treating pelvic conditions and, more particularly, systems and methods to support pelvic tissue by acting on, stabilizing, positioning or controlling the position of the perineal membrane or like anatomical structures.

BACKGROUND OF THE INVENTION

It has been reported that over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. The urethra is the tube that passes urine from the bladder out of the body. The narrow, internal opening of the urethra within the bladder is the bladder neck. In this region, the bladder's bundled muscular fibers transition into a sphincteric striated muscle called the internal sphincter. The urethra extends from the bladder neck to the end of the penis. The male urethra is composed of three portions: the prostatic, bulbar and pendulus portions. The prostatic portion is the widest part of the tube, which passes through the prostate gland. The rectum is the most distal portion of the gastrointestinal tract. The exterior opening of the rectum is the anus. Fecal continence is related to control of the exterior sphincter and interior sphincter of the anus.

Urinary incontinence may occur when the muscles of the urinary system are injured, malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder," "frequency/urgency syndrome," or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

SUI is generally thought to be related to hypermobility of the bladder neck or an intrinsic urethral sphincter defect. A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of SUI can include lifestyle changes, such as weight loss, smoking cessation, and modification of intake of diuretic fluids such as coffee and alcohol. Midurethral slings have been effective. One type of procedure, found to be an especially successful treatment option for SUI in both men and women, is a sling and support procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension structures or sutures to a point of attachment (e.g., tissue or bone) through an abdominal and/or vaginal incision. Examples of sling procedures are disclosed in U.S. Pat. Nos. 5,112,344; 5,611,515; 5,842,478; 5,860,425; 5,899,909; 6,039,686, 6,042,534, 6,110,101, 6,911,003, 6,652,450, and International PCT Publication No. 2008/057261, all of which are herein incorporated by reference in their entirety.

Fecal incontinence, like urinary incontinence, has proven to be challenging to treat. Patients whose fecal incontinence is caused by external anal sphincter injury is treated surgically, as with a sphincteroplasty. Other patients, though, are considered to have neurogenic or idiopathic fecal incontinence, and efforts to treat these patients has been less successful. Various procedures, such as postanal repair, total pelvic floor repair, muscle transposition techniques, dynamic gracilo-plasty, artificial sphincter procedures, and sacral nerve stimulation. Success has been limited, and the various treatment modalities can result in morbidity.

There is a desire for a minimally invasive yet highly effective treatment modality that can be used with minimal to no side effects for the treatment of both urinary and fecal incontinence. Such a modality should reduce the complexity of a treatment procedure, be biocompatible, should reduce pain, operative risks, infections and post operative hospital stays, and have a good duration of activity. Further, the method of treatment should also improve the quality of life for patients.

SUMMARY OF THE INVENTION

The present invention can include surgical instruments, implantable articles, and methods for urological applications, particularly for the treatment of stress and/or urge urinary incontinence, fecal incontinence, and prolapse by implanting a paraurethral constraining device. The constraining device or implant can control and eliminate rotation of the urethra that is associated with incontinence.

Embodiments of the present invention can include apparatus and methods for treating urinary incontinence, fecal incontinence, and other pelvic defects or dysfunctions, in both males and females using one or more implants to reinforce the supportive tissue of the urethra. The implants are configured to engage and pull (e.g., pull up) or reposition the supportive tissue, such as the perineal membrane. The perineal membrane is the fibrous membrane in the perineum that intersects the urethra and vagina near the midurethra location and can thus be stabilized or controlled in a manner that helps restore continence. As such, systems, methods and implants can be utilized to eliminate the need for mesh or other supportive structures under the urethra that is common with other incontinence slings. The implants can be shaped to facilitate such support, e.g., provided with anchoring end portions, barbs or other devices of many available shapes and configurations. One or more anchors or tissue engagement portions can be employed to attach and stabilize the implants or devices to tissue.

Embodiments of the present invention can provide smaller implants or devices, fewer implant or device components, thus reducing the size and number of incisions, improving implant manipulation and adjustment, the complexity of the insertion and deployment steps, and healing times.

The implants can resist movement of tissue such as, for example, forward rotational movement of the urethra or surrounding tissue. The present implant embodiments can utilize a perineal incision or puncture and a paraurethral constraining device. Alternatively, the device may be implanted transvaginally.

In certain embodiments, one or more paraurethral support devices are provided. Paraurethral suspension elements are provided for the treatment of SUI and other disorders. The support, extension or suspension elements can apply mechanical traction to the urethra in a manner similar to a mini-sling device, wherein tension is applied at the midurethral position to lift and support that anatomical structure during stress events, such as coughing or physical activity.

An anchoring element or portion, such as a medial or proximal anchor, is fixed on each side of the urethra on the far side of a tissue layer that is known to have relatively high strength and toughness. Such anatomical structures can include the uterovaginal fascia, endopelvic fascia, perineal membrane or other anatomical features at which connective support of the urethra can be established. The medial anchor can include a self-expanding anchor, a "toggle" anchor, which is a small elongated structure that can be placed through the tissue via a small puncture or like incision and then rotates after deployment so that it cannot back out through the incision hole, or a myriad of other anchoring and tissue engagement devices.

Placing the medial anchor device on the far side of the fascia is advantageous because it is less likely to be palpable than one placed in the mucosal and muscle layer. It can be placed in an area of loose connective tissue in which the anchor can easily rotate or expand into a locking or engaging orientation.

A second anchor device, such as a distal anchor or engagement device, is placed in a lateral or superior position such that a connection between the medial and lateral anchors (via a suture, mesh, wire or like connection) can provide tensile support for the urethra during stress events. The distal anchor device can be fixated to, or around, the tendinous arch of the levator ani (white line), the Cooper's ligament, the obturator foramen, obturator internus, abdominal fascia, sacrospinous ligament, prepubic fascia or muscle, the pubic symphysis cartilage, or other stable anatomical structures. The distal anchor devices can include a body portion, a beveled tip, one or more expandable barbs, a thru-aperture, and an opposing end. The suture or like extension member is adapted to string or thread through the respective apertures of a series or array of such anchors. The array of anchors can be inserted within and along the interior lumen of a needle, cannula or like inserter or delivery tool for deployment. In addition, the distal anchor, or anchor array, can be directed down below the urethra for fixation, to provide an alternate control over the position and rotation of the urethra.

The final position of the implanted device creates a support structure that can include a generally straight, suspension orientation. The medial anchor can spread or better distribute the tension load over a larger surface compared to a thin suture cutting edge surface. This, in turn, promotes stability of the anchor and connecting suture and, ultimately, the target support tissue.

Various procedural steps or methods can be implemented to deploy and anchor the implant of the present invention. In one embodiment, the medial anchor is implanted, a needle is withdrawn, a free suture or connector end is delivered through the insertion opening, the second distal anchor is delivered and implanted, and the connecting suture is properly tensioned between the anchors to provide proper support. The suture or other support extensions members can be constructed to be generally flexible, or to have limited elasticity—e.g., bungee-type attributes.

Various anchoring systems, device, techniques and placement locations are provided to facilitate the support and rotational prevention of exemplary embodiments, as well as hingable anchor constructs and configurations, as well as suture pathways and anchoring positions.

A benefit of certain embodiments of the present invention is that a transvaginal placement of the support devices does not leave exposed material inside the vaginal cavity. For example, the final device position can be completely blind, beyond the superficial mucosal layer of the vaginal wall. Reducing or eliminating the exposed material minimizes the risk of infection, irritation at the surface of the vaginal wall, and provides cosmetic improvement and reduces interference with sexual activity.

BRIEF DESCRIPTION OF THE DRAWINGS

FIG. 7 shows a side view of an implant system having medial and lateral anchors, and sutures, in accordance with embodiments of the present invention.

FIG. 8 is a top view of an implant system having medial and lateral anchors, in accordance with embodiments of the present invention.

FIG. 26 is a side schematic view of a medial anchor and suture, with the medial anchor expanded and deployed from a delivery tube or oversleeve, in accordance with embodiments of the present invention.

FIG. 27 is a perspective schematic view of a medial anchor and suture, with the medial anchor expanded and deployed from a delivery tube or oversleeve, in accordance with embodiments of the present invention.

FIGS. 43-45 are schematic views of a grasping medial anchor device, and implantation method, in accordance with embodiments of the present invention.

FIGS. 46-47 are views of a generally star-shaped medial anchor device, in accordance with embodiments of the present invention.

DETAILED DESCRIPTION OF PREFERRED EMBODIMENTS

Figure 1:
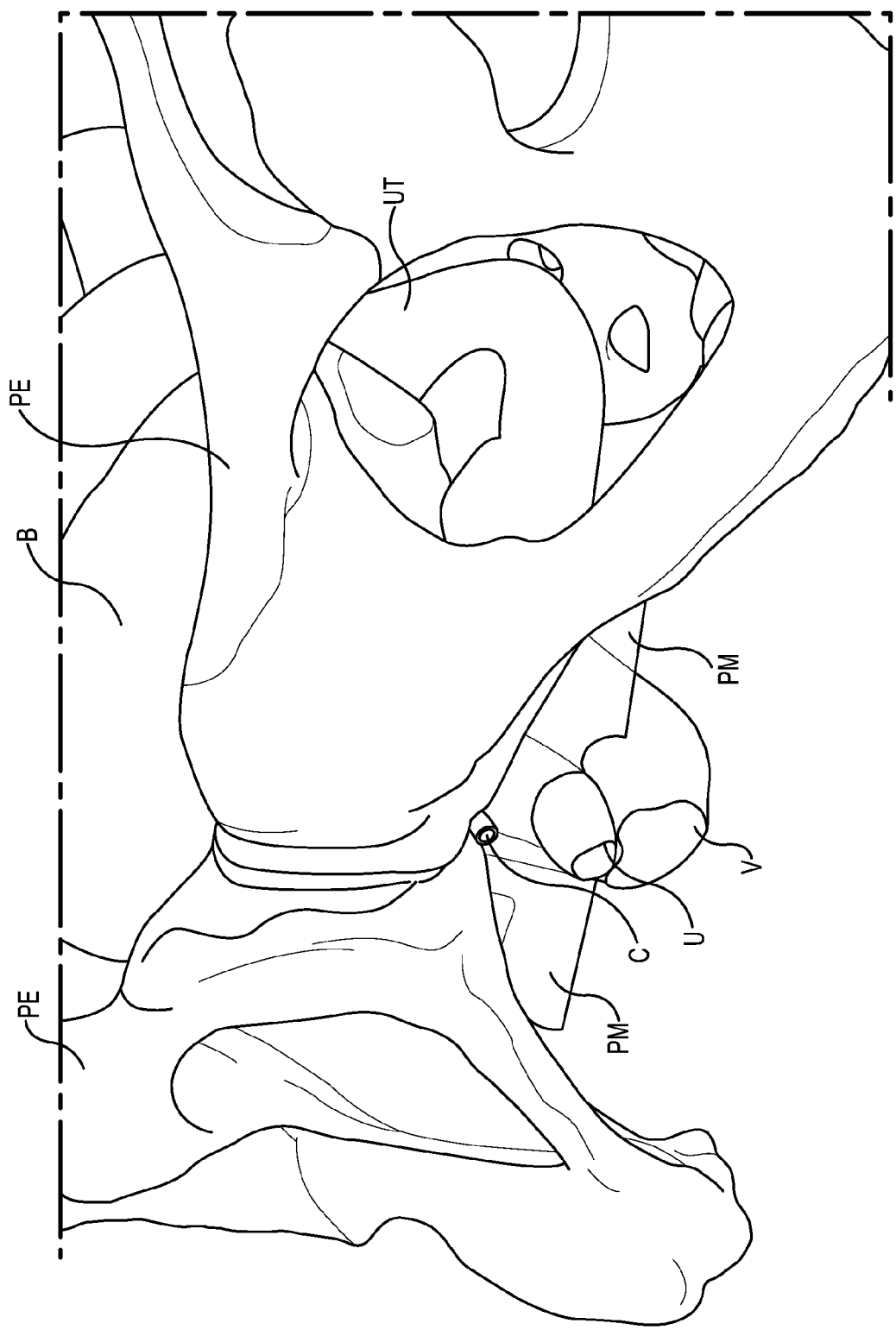
FIG. 1 is a schematic view of various anatomical structures of the female pelvic region, including urinary and reproductive systems.
Figure 2:
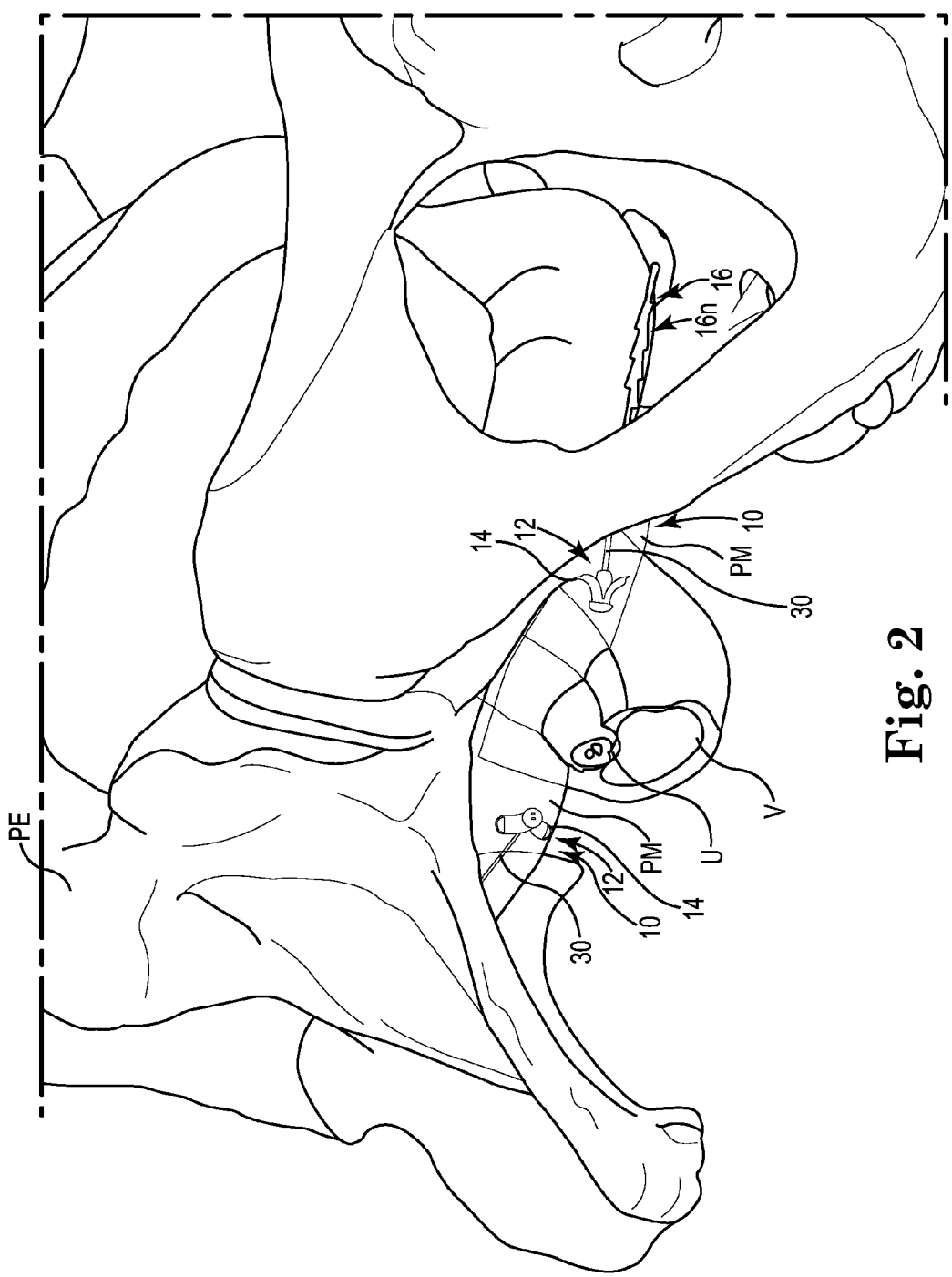
FIGS. 2-6 are schematic views of various anatomical structures of the female pelvic region, and bilateral implants having medial and lateral anchors, in accordance with embodiments of the present invention.
Figure 3:
Figure 4:
Figure 5:
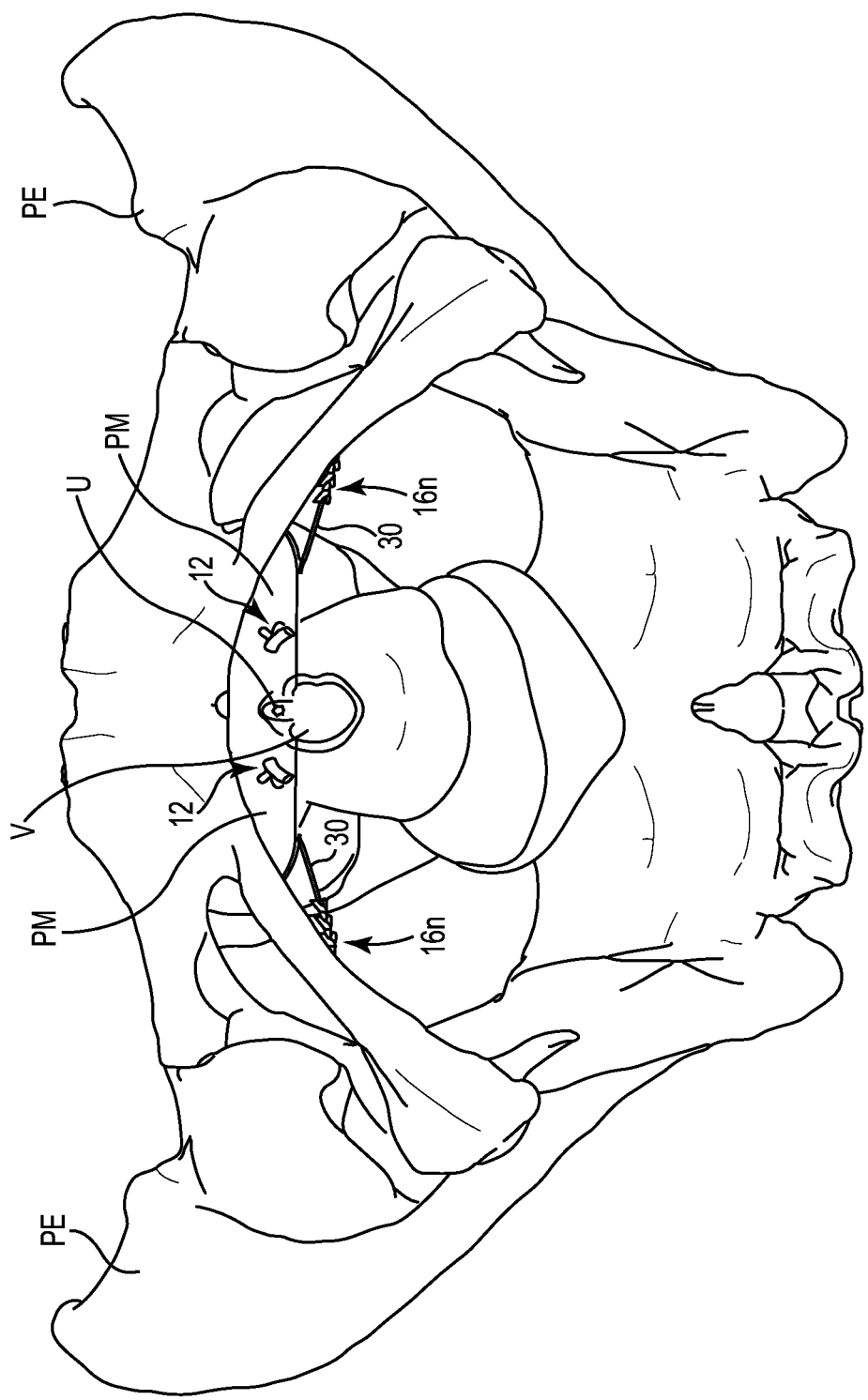
Figure 6:
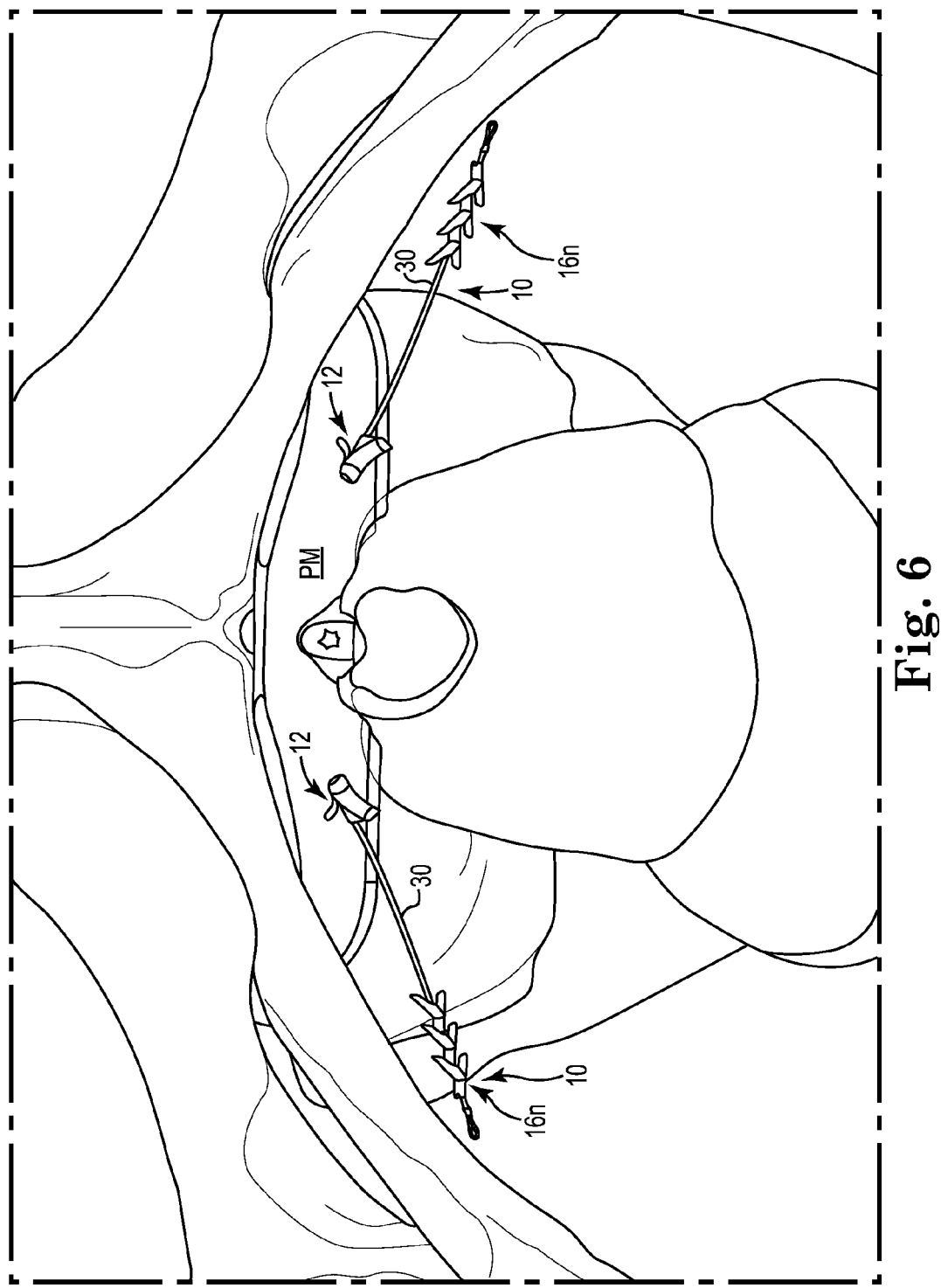
Figure 9:
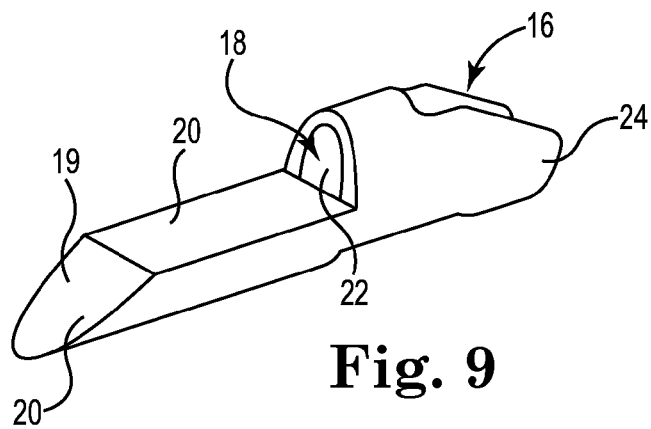
FIG. 9 is a perspective view of a distal anchor/barb in accordance with embodiments of the present invention.
Figure 10:
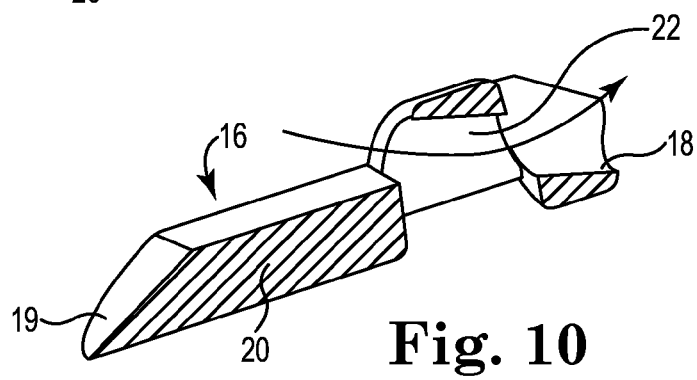
FIG. 10 is a partial sectional view of the distal anchor/barb of FIG. 9.
Figure 11:
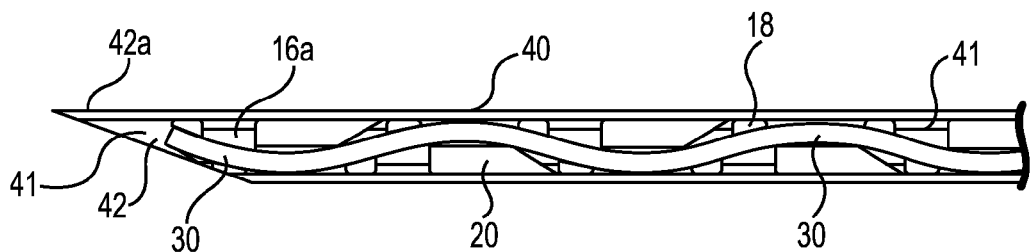
FIG. 11 is a side schematic view of a distal anchor array and suture within a delivery needle device, in accordance with embodiments of the present invention.

FIG. 1 shows a schematic view of relevant portions of the female pelvic region, and the urinary and reproductive system, including the pelvis PE, vagina V, uterus UT, urethra U, bladder B and the deep clitoral vein C. Further, a portion of the perineal membrane PM is shown at the midurethra/distal location, providing a viable paraurethral target for stabilizing or controlling the position and movement of the urethra to assist in restoring continence.

Embodiments of the present invention can include apparatus and methods for treating urinary incontinence, fecal incontinence, and other pelvic defects or dysfunctions, in both males and females using one or more lateral implants to reinforce the supportive tissue of the urethra. One or more implant devices 10 are configured to engage and pull (e.g., pull up) or reposition support tissue (e.g., paraurethral), such as the perineal membrane, uterovaginal fascia, endopelvic fascia, or other anatomical features at which connective support of the urethra can be established. The perineal membrane intersects the urethra and vagina at the midurethra/distal location and can thus be stabilized or controlled in a manner that helps restore continence. As such, the implants 10 can be utilized to eliminate the need for mesh or other supportive structures under the urethra that is common with other incontinence slings. The implants can be shaped to facilitate such support, e.g., provided with anchoring end portions 12, barbs or other devices of many available shapes, sizes and configurations, and extension members 30.

Various embodiments of the extension members 30 can be constructed of a suture, a thin flat member, braided fibers, braided nano-fibers, an elongate mesh and other various materials and constructs. For those embodiments including braided nano-fibers, the extension member 30 can enhance and draw more collagen-producing cells to the material to promote tissue ingrown and healing. The extension member 30 of certain embodiments of the present invention can be constructed to be generally flexible, or to have limited elasticity—e.g., bungee type attributes. For instance, the member 30 extending between the anchors 14 and anchors 16 can be an elongate member constructed of an elastomeric material having desirable tensile properties. As such, the member 30 can be stretched out for deployment and then released to provide desirable taut tension. The travel or stretching/rebound characteristics of the member 30 can vary depending on the particular elastomeric materials used in its construction. The extension member 30, such as a suture, can further include various extending tines or barbs to facilitate the tissue traction and grabbing during and after deployment.

One or more opposing anchors 14, 16 or tissue engagement portions can be employed to attach and stabilize the implants to the tissue, as well as provide selective adjustment. The anchors or engagement portions can be configured to engage soft tissue and can include various barbs, tines, serrated edges, extending fibers, or other similar structural feature to promote tissue fixation. The anchors can be implanted in a direction lateral from the urethra. The anchors can generally be small enough for to be unnoticeable by both the patient and the patient's sexual partner. The anchors and other devices and components of the system 10 may be constructed from various biocompatible materials, such as known polymers and metals that promote long-term resilience, or other materials known to those skilled in the art.

In various embodiments, the one or more implants 10 can be placed in strategically located positions to pull up or otherwise tighten tissue and/or muscle lateral or otherwise intersecting or attached (directly or indirectly) with the urethra to generally stabilize the anatomical structure of the patient. Various systems, devices, structures, techniques and methods, alone or in combination, as disclosed in U.S. Pat. Nos. 7,500,945, 7,407,480, 7,351,197, 7,347,812, 7,303,525, 7,025,063, 6,911,003, 6,691,711, 6,648,921, 6,612,977, 6,802,807, 2002/0161382, 2002/0147382, 2002/151762, 2004/0039453, 2008/0057261, 2008/0045782, 2010/0105979, 2011/0144417, and 2011/0201876 and International PCT Publication Nos. WO 2008/057261 and WO 2007/097994, can be employed with the present invention, with the above-identified disclosures being incorporated herein by reference in their entirety. The devices or structures described herein can be employed or introduced into the pelvic region of the patient transvaginally, percutaneously or in any other manner known by those of ordinary skill in the art.

Referring generally to FIGS. 2-6, various embodiments are shown of the tissue constraining or positioning implant system 10 having one or more attachment points in one or more membranes or other target tissue locations. Embodiments can function to restrict, limit or control movement of the mid or distal urethra, or surrounding tissue. Further, embodiments can assist in resisting forward rotational movement of the urethra or surrounding tissue, and can provide support and tension during events, such as coughing or physical activity. Various advantages of the implant 10 embodiments depicted herein include, frontal access and simpler anatomy to address, less vascularity and bleeding, reduced risk of creating retention and de novo urge, and the ability to test for continence before surgery. Additionally, the implants 10 act to oppose rotational movement of the urethra, thereby eliminating or lessening the effects of stress urinary incontinence.

A viable treatment, therefore, will be one that most efficiently opposes rotational movement of the urethra. Urethral rotation still occurs in non-hypermobile patients, just to a lesser extent. The concept of rotational mechanics also suggests that obturator anchored implants should be placed with higher initial tension and be positioned as far distally as possible on the urethra. Applying this principle of rotational resistance gives rise to devices in accordance with the present invention whereby urethral movement is inhibited near the distal urethra, while the bladder neck continues to move.

When a midurethral support is implanted in the female patient, the midurethra is restrained from movement. However, the bladder neck remains mobile and moves downward during a stress event due to elevated abdominal pressure. The resultant effect is that the urethra can be kinked at the midurethra location, causing a closure of the urethra. Like kinking a garden hose, the flow of fluid is restricted or prevented.

Referring again to FIGS. 2-8, the implant system 10 can include one or more anchor devices 12 adapted for use with various embodiments of the present invention, including those adapted to penetrate tissue or soft tissue as disclosed herein. Certain of the devices 12, e.g., the lateral anchor 16, can be generally provided in a back-to-back serial configuration, with a suture or like extension member extending to provide adjustable support between the anchor devices 12. As shown in FIGS. 7-8, the anchor devices 12 can include one or more first medial or proximal anchor devices 14, and one or more second lateral or distal anchor devices 16.

Referring generally to FIGS. 9-23, the lateral anchor devices 16 can include a body portion 18, one or more expandable barbs 20, a thru-aperture 22, and an opposing end 24. A suture 30 or like member is adapted to string or thread through the respective apertures 22 of a series or array 16n of such anchors to define the general elongate and expandable configuration shown. The array of anchors 16n can be inserted within and along the interior lumen 41 of a needle 40, cannula or like inserter or delivery tool.

In various embodiments, the lateral anchor devices 16 can be directed for engagement with tissue distal the anchors 14 at target sites such as the obturator foramen, obturator internus muscle, sacrospinous ligament, prepubic fascia or muscle, abdominal fascia, rectus fascia, puboprostatic ligament, the tendinous arch of the levator ani, the Cooper's ligament, and the pubic symphysis. Other distal target tissue sites for the anchors 16 capable of permitting tensioning support for the perineal membrane or other urethra-supporting tissue is envisioned as well. Unlike conventional sling device and implantation methods, the path from the perineal membrane to the distal anchor 16 of the present invention can follow a generally straight line into the obturator internus muscle, or like distal tissue. Furthermore, because it intersects the muscle at an oblique angle, more tissue can be engaged for securement.

Figure 12:
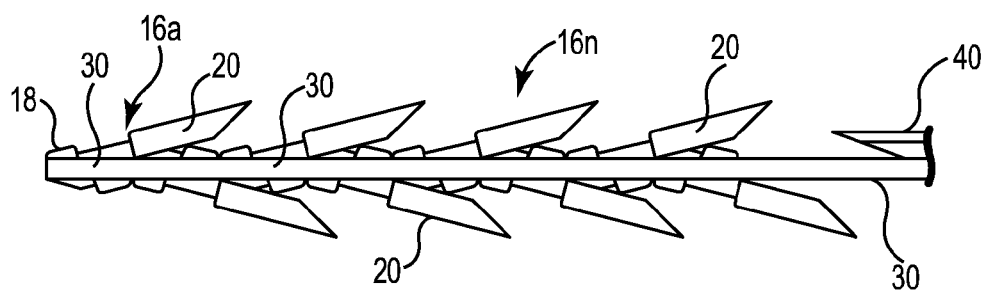
FIG. 12 is a side view of a distal anchor array and suture deployed from a delivery needle device, in accordance with embodiments of the present invention.
Figure 13:
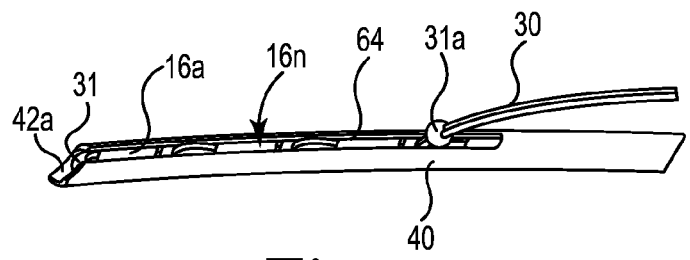
FIG. 13 is a perspective view of a distal anchor array and suture within a slotted needle device, in accordance with embodiments of the present invention.
Figure 14:
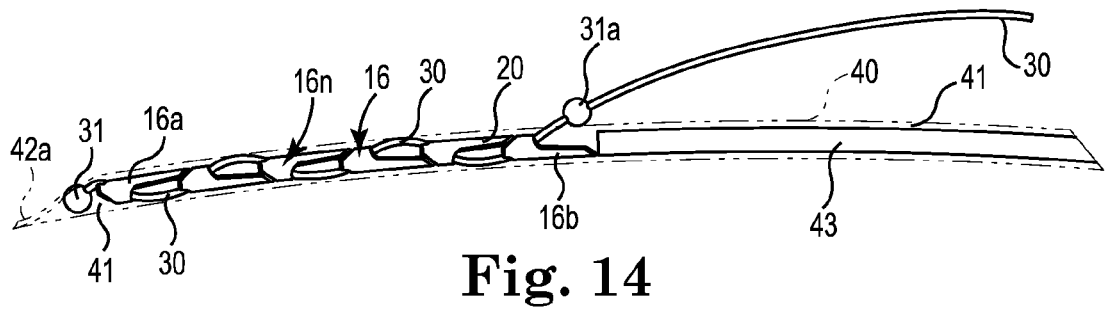
FIG. 14 is a side schematic view of a distal anchor array and suture within a slotted needle device, in accordance with embodiments of the present invention.
Figure 15:
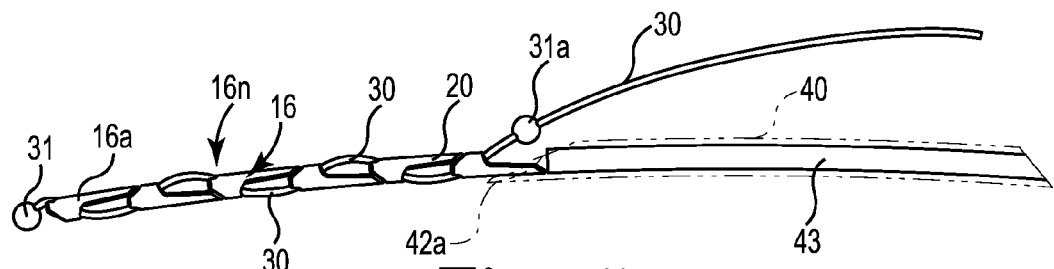
FIG. 15 is a side view of a distal anchor array and suture deployed from a slotted needle device, in accordance with embodiments of the present invention.
Figure 16:
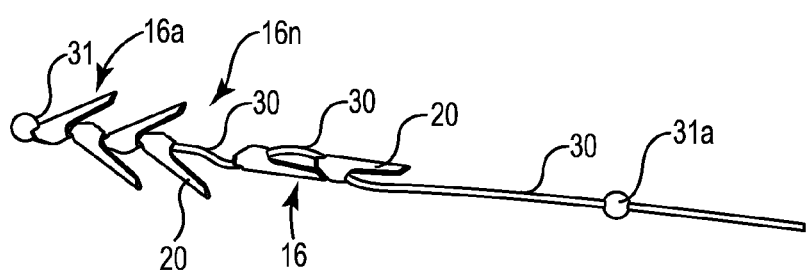
FIG. 16 is a side view of a distal anchor array and suture at least partially tensioned, in accordance with embodiments of the present invention.

Referring generally to FIGS. 11-16, the needle 40 can include an exit or opening 42 at a needle tip 42a. A series of anchors 16, such as the anchor array 16n, can include a lead anchor 16a adapted to first exit through the opening 42 upon deployment. In certain embodiments, the suture 30 path is generally undulating while within the needle 40, and even upon initial departure from the needle 40 (FIGS. 11 and 13-15), while it is generally brought into a straight or taut state upon full deployment from the needle 40 (FIGS. 7, 12 and 16). The end portion 24 of the lead anchor 16a can be permanently attached to the end of the suture 30 via bonding, adhesive, welding, knotting, or the like. The anchor 16 or its respective components can be molded together or otherwise attached to create the construct depicted and disclosed.

Each successive anchor 16, e.g., after lead anchor 16a, is alternately arranged such that they can be closely aligned along or within the lumen 41 of the delivery needle 40. The suture 30 passes through these anchors 16, and the anchors 16 can be adapted to slide on the suture 30. Again, when the anchor array 16n is inside the needle 40, the suture 30 can follow a serpentine or otherwise undulating path. A pusher rod 43, or like mechanism or device may be biased or pushed against the proximate anchor 16b (e.g., opposite end from the lead anchor 16a), as illustrated in FIGS. 14-15, such that the array of anchors 16n pushes against the distal end, or lead anchor 16a, that is fixed to the suture 30. This can help maintain the close alignment of the anchors 16 while inside the lumen 41 of the needle 40 and thus facilitate deployment.

When the delivery needle 40 is at the intended anchor position or target tissue, the array 16n can be deployed in various ways. In one method, the pusher 43 simply forces the anchors 16n out of the lumen of the needle 40. Some suture 30 tension can be maintained so that the anchors 16n are efficiently driven out in a straight line or path. In another method, the position of the anchors 16n relative to the tissue remains fixed or stationary (e.g., with the aid of the pusher 43) while the needle 40 is retracted back or away (e.g., slid) from the array 16n such that the anchors 16 are deployed from the lumen 41. With either approach, after the array of anchors 16n is completely outside the needle 40, tension can be applied against or upon the suture 30. This forces the individual anchors 16 to slide together and tilt outward at an angle relative to the suture while they embed into the tissue, creating firm engagement. The tilt angle, relative to a straightened suture, ensures engagement into tissue and is preferably 25 to 45 degrees. The pusher rod or member 43 can be a wire or tube that fits inside and through the proximal end of the needle 40, through the lumen 41, and acts against at least one of the anchors, directly or indirectly, including the most proximal anchor.

Figure 18:
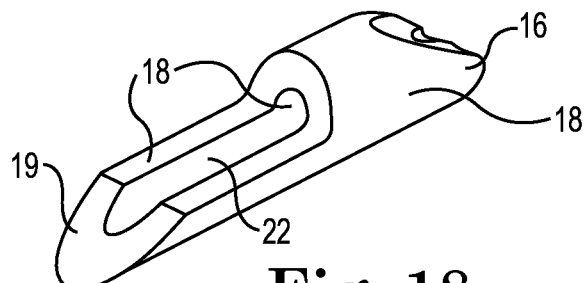
FIG. 18 is a perspective view of a distal anchor/barb in accordance with embodiments of the present invention.
Figure 19:
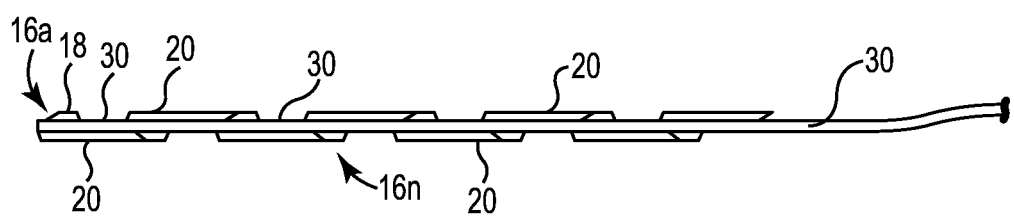
FIG. 19 is a side view of distal anchor array and suture in a collapsed state, in accordance with embodiments of the present invention.
Figure 20:
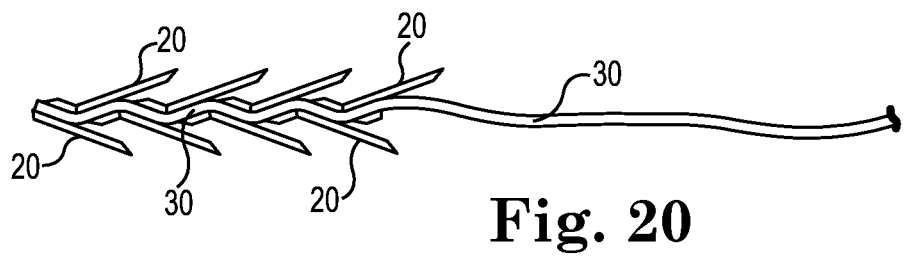
FIG. 20 is a side view of a distal anchor array and suture in an expanded state, in accordance with embodiments of the present invention.

Other embodiments of the anchor 16, as shown in FIGS. 18-20, can include an extended thru-aperture 22, generally along the length of the body 18 of the anchor 15, that allows the suture 30 to pass in a generally straight line through the array 16n while in the lumen 41 of the needle 40, and bend or reform into a general serpentine or undulating shape after the anchors 16 have been deployed and the barbs 20 expand outward for tissue engagement. This approach can have the advantage of utilizing the suture 30 tension to resist the rotation of the barbs 20 working against tissue.

Figure 21:
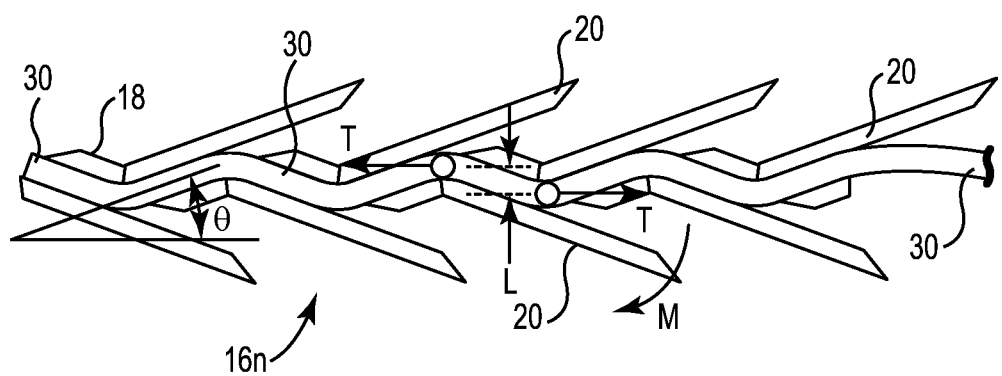
FIG. 21 is a side view of a distal anchor array and suture, showing exemplary load and moment data, in accordance with embodiments of the present invention.

Referring generally to FIG. 21, and various embodiments, when the barbs 20 are engaged within the target tissue site, they can be subjected to a moment load M. This moment is opposed by the suture line tension moment which is proportional to T*L, where T is the tension and L is the moment arm. This moment arm increases as the angle θ of the serpentine or undulation increases. Thus, such a configuration during initial application of tension is better able to work in the tissue than one in which the suture is in a straight line (θ=0) after anchor deployment. By controlling the serpentine angle in the barb design, the effectiveness of the anchor array 16n may be optimized. The bending stiffness of the suture 30 will also affect the rotational resistance, and a solid suture 30 will have more bend stiffness than a braided one of similar material.

Figure 22:
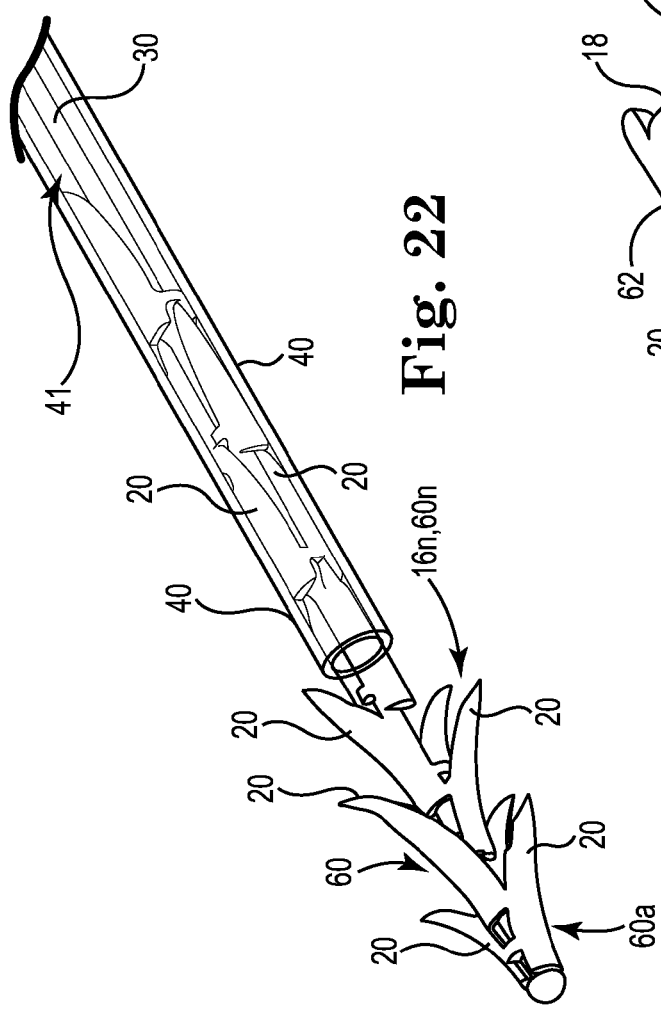
FIG. 22 is a perspective schematic view of a distal anchor array, with dual barbs, and a suture partially within a needle device, in accordance with embodiments of the present invention.
Figure 23:
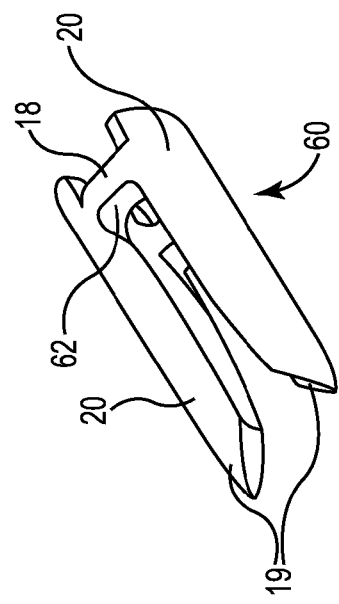
FIG. 23 is a perspective view of a distal anchor, or anchor portion, having dual barbs, in accordance with embodiments of the present invention.

Another embodiment of the anchors 16 and anchor array 16n configuration is provided in FIGS. 22-23. A dual-tipped/barbed anchor 60 is included that flexes about a hinge 62 at the base 18. Again, the anchors 60 are provided in an array 60n with a lead anchor 60a. The array of barbs 16n are spaced apart along the suture 30 while inside the lumen 41 of the needle 40, and condense or compress together as they are pushed out of the needle 40, or the needle 40 is removed, and put under tension. The two barbs 20 of each anchor 60 are forced further open by the body portion 18 of the adjacent abutting anchor 60. For instance, the body portion 18 of the preceding anchor 60 can slide into the gap between the two barbs 20 of the next leading anchor 60 to cause those barbs 20 to flare out or expand, as shown in FIG. 20. This configuration may be more compact than the single barb designed anchor 16 and also may not depend as much on the suture 30 tension to oppose the load on the tips. Namely, the tissue fixation may better resist backing out of the tissue target site compared to various other embodiments for cases where an increased degree of fixation is required or desired.

In certain embodiments, the anchors 16, or anchors 60, can be fabricated using a metal injection molding process, or from a molded resin material (e.g., 720FC resin, polycarbonate, PEEK, nylon), with an exemplary Prolene monofilament, or braided, suture 30 threaded therethrough. The components can be easily inserted through the lumen 41 of the needle 40 and arranged in an alternating pattern—e.g., angular orientation pattern—along the suture 30. For instance, the alternating angular pattern of the anchors 16 in FIG. 7 is approximately 180 degrees, whereas the alternating angular pattern of the anchors 60 in FIG. 22 is approximately 90 degrees. Of course, a myriad of alternate angular patterns and orientations are envisioned for embodiments of the invention depending on the particular deployment, anchoring and engagement needs. The suture 30 can be lightly tensioned to bring all the anchors 16 in the array 16n together while holding the pusher 43 in place. Again, while holding the pusher 43 stationary, the needle or cannula 40 can be retracted, leaving the array 16n, or 60n, and the respective anchor barbs 20 embedded in tissue. A slight tug of the suture 30 can bring the anchors together and take up any initial slack in the suture line 30.

As shown in FIGS. 7-8, embodiments of the tissue anchoring devices and methods can include a reduced trauma explantation (e.g., removal from tissue) configuration and mechanism for the barbed soft tissue anchors, e.g., the anchors 16, described and depicted herein. For instance, one solution is to attach an explantation tether 50 to the leading anchor 16a of the array 16n. This could be in the form of a suture, or continuation of the existing traction suture 30 that leads back out of the implantation path. To remove the anchor 16, or anchor array 16n, the physician simply pulls on this tether 50, causing the anchor 16 to double-back on itself and pull out atraumatically—e.g., through the defined tissue path or tissue penetration site. This could be done during the initial implantation procedure or at a later time in the event that the device 16, or implant 10, must be disengaged or removed.

The average normal pullout force of an engaged anchor 16 or anchor array 16n can be approximately 4 to 7 lbs with various embodiments, while the explantation force of the embodiments having the explantation tether 50 can be around 1 to 3 lbs. By leaving a segment of loose tether 50 attached to the leading anchor 16a, the physician can pull out the entire assembly by tugging on it. Pulling up on the explant suture or tether 50 causes the anchors to double-back on themselves and continue out of the tissue in the non-resistant direction, lead by anchor 16a. This reduces the removal force and associated tissue trauma. This type of explant method can be used with any implanted device that has an anchoring end that is generally flexible or segmented enough (e.g., series of separate anchors 16 strung along the member 30 of the anchor array 16n) to allow doubling-back. The implant can be designed such that the free end of the explant tether 50, generally opposite the end attached to or proximate the lead anchor 16a, can be accessed by a physician. This could be done by leaving the suture 50 end hanging out of the implantation puncture. The free end can be later trimmed or removed when explantation is no longer needed. In various embodiments, the tether 50 can be constructed of an absorbable material. Alternatively, a tag or loop can be included at the free end of the tether 50. This tag or loop can remain just below the skin surface and can be accessed later if the implant 10 or device 16 require explantation.

The anchor array 16*n* is thread or otherwise provided along the suture 30, or paired sutures 30 (e.g., FIG. 17), and can be delivered via a percutaneous passage inside a hypotube or the needle 40. This allows for controlled delivery of the anchor array 16*n* such that the needle tip 42*a* can be selectively repositioned before the anchors are set in soft tissue.

Referring generally to FIGS. 13-16, embodiments of the needle system 40 can include a slotted needle configuration, with the needle 40 including a slot or groove 64 along a distal or end portion of the needle 40 body such that a portion of the suture 30 can pass outside the lumen 41 of the needle 40 during deployment. The slot 64 can be created in or along a portion of the needle 40 by milling, laser cutting, EDM machining, or using other similar fabrication, manufacturing or formation methods. For needles 40 requiring some curvature to facilitate use and deployment, the slot machining may be done before or after the bending operation for the needle 40. With a curved needle 40, the slot 64 can be on the outer side of the bend. This, in turn, can promote keeping the portion of the suture 30 that lies in the slot 64 to stay inside the lumen 41 when under tension.

Figure 17:
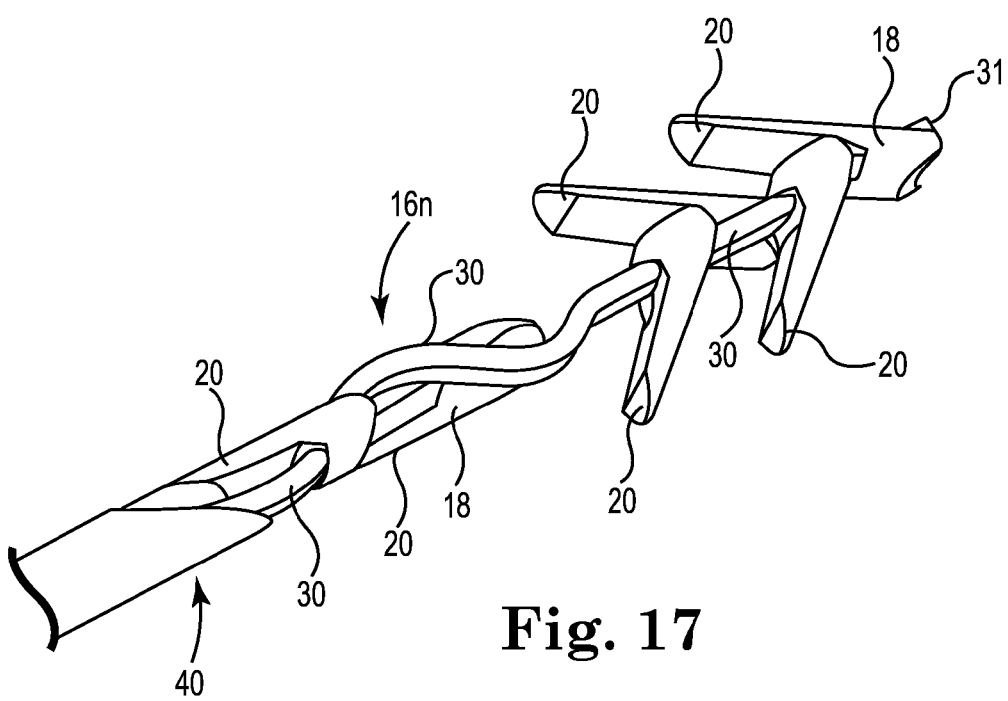
FIG. 17 is a perspective view of a distal anchor array and dual suture, in accordance with embodiments of the present invention.

As described, a pair of sutures 30, e.g., FIG. 17, can pass through each anchor 16 in the array 16*n*, and follow a serpentine or undulating path within the needle 40. A knot, bead, stop, member or like structure 31 at the distal end of the suture 30 proximate or in front of the leading anchor 16*a* can act as a stop for the lead anchor 16*a*. A second knot, bead, stop, member or like structure 31*a*, can be included at a portion of the suture 30, or paired suture, near the most proximal anchor 16*b*, and/or outside the slot 64 (e.g., FIGS. 13-14).

Embodiments employing a paired suture 30 configuration can include members, structures or other constructs, including the apertures 22 of the anchors 16, having a generally rectangular or oval shape such that the pair can be passed through to hold them side-by-side. By doing this, the barbs 20 are less able to rotate on the axis of the suture line 30 and will stay properly oriented. By creating anchors 16 that have different through hole angles or shapes it is also possible to fix the angular position of the anchors 16*n* to create a larger anchor spread.

Again, a pusher 43 can be positioned behind, or abut against, the proximal anchor 16*b* that acts as a stop (prevent backing out of array 16*n* within needle lumen 41) during the needle insertion and deployment process. The pusher 43 can also serve to maintain the anchors 16 and respective barbs 20 barbs in a fixed position, relative to the tissue, as the needle 40 is retracted or pulled away from the array 16*n*. The slot 64 can be sized to allow the suture 30 to freely pass through, but does not allow the anchors 16 or respective barbs 20 out through that portion of the needle 40. The length of the slot 64 can assume many size configurations, depending on the size of the anchors 16 in the array 16*n* and the number of serially aligned anchors 16 in the array 16*n*. However, the slot 64 could also extend along the entire length of the entire needle 40 in certain embodiments, or take on various other size and shape configurations depending on particular device and application needs. Moreover, the slot 64 length can be defined by the anticipated length of depth of the tissue targeted for penetration.

Further, embodiments of the needle 40 including the slot 64 configuration can facilitate easier and more efficient use of a medial anchor 14. The medial anchor 14 is attached to, or threaded or provided along a portion of the suture 30 that does not need to be constrained or fit within the relatively thin and small needle 40 or lumen 41. As such, the slot 64 provides a length of suture 30 that can ride outside of the lumen 41, with the medial anchor 14 attached or provided along that external length of suture 30. This provides greater flexibility for the design and construct of the medial anchor 12 and the respective delivery method. In addition, the pusher 43 will not interfere (e.g., traverse alongside) with the proximal length of the suture 30 provided before the anchor array 16, as the proximal portion of the needle lumen 41 will be free of the suture 30. Also, there can be a reduced tendency for the anchors 16 to wedge together and jam if subjected to excessive push forces because the slot 64 provides more room for movement and spreading compared to non-slotted embodiments of the needle 40 where everything within the lumen 41 is confined to the lumen walls. Still further, the slot 64 keeps the exiting suture 30 portion from unwanted turning and twisting, thereby assisting in keeping the attached anchors 16 also fixed in a preferred angular orientation within the needle 40.

The proximal stop 31*a* can also be used to keep the anchor barbs 20 from spreading apart during assembly and during the deployment of the anchors 16*n*. With the slotted needle 40, the knot, bead or stop 31*a* can be positioned either inside or outside the lumen 41. One advantage for positioning the stop 31*a* outside is that it can introduce enough drag to enable retraction of the needle 40 while still keeping the anchors 16 in place. In certain embodiments, this can preclude the need for an internal pusher 43 to hold the anchors 16 in place upon deployment. The stop 31*a* could take on nearly any size or shape, and material. Also, the anchor system can include intermediate knots, beads or stops 31 that separate smaller or distinct groupings of anchors 16. For example, a stop 31 between a fourth and fifth anchor 16 can result in two groups of four barbs forming on the suture line 30. Such a grouping configuration can assist in redistributing the tension on the suture line 30 in stages or segments, as well as to reduce the amount of pulling that is required to initially set the anchors 16 in tissue. It can also improve the overall tissue anchoring force and stability.

Embodiments of the lateral anchors 16 can include self-expanding structures or materials such that the anchors 16, or anchor array 16*n*, can be generally collapsed or reduced in sized during deployment, with or without a needle device 40, and expanded after penetration in the target tissue site to provide desired tissue engagement. Certain anchors 16 can include one or more shape memory portions, or living hinges, to facilitate this structural self-expansion upon deployment and tissue engagement. Further, embodiments of the lateral anchor 16, or anchor array 16*n*, can include helical portions, threaded portions, hooks, clips, flexible barbs, textured surfaces, and like members or structures to promote tissue engagement. In addition, still other embodiments of the lateral anchor 16 can be adapted to include a plurality of anchors, extending from one or more separate members 30, spread out into multiple anchoring features for deployment into tissue to provide support and treatment. Such a spanning multi-anchor device 16 can create a neo-ligament to reduce or eliminate rotation of the urethra U or surrounding tissue through the use of multiple anchoring spots.

As shown in FIGS. 24-27, the medial anchors 14 can include metal or like members or tubing, such as nitinol, stainless steel, titanium, or polymer, laser cut or formed into longitudinal petals 44 that are capable of selectively collapsing and expanding in a flex leaf construct. The cutting may be done such that any number of petals is formed. Exemplary embodiments can include two, three or four petal constructs.

In certain embodiments, the formation and configuration of the petals 44 can be accomplished using a heat-treatment process where the petals 44 are set in the opened state, and whereby the ends of the petals 45 a distance from the hinges 48 are radially expanded and set in that position. However, due to the elasticity or hingability of the material, these petals 44 can be temporarily closed, facilitating the insertion of the anchor 14 into a small puncture, such as within the tissue of the perineal membrane PM. Once positioned, the anchor 14 can self-expand, e.g., via shape memory, to the opened state to provide tissue engagement and fixation.

Various embodiments of the medial anchors 14 can include slots 49 (e.g., laser cut) in the petals 44 to develop the bend or living hinges, as shown in FIGS. 26-27. These slots 49 can be very narrow (e.g., approximately 0.001"-0.003" wide) and allow a limited degree of localized bending along a portion of the corresponding petal 44. As a result, the petals 44 can easily flex to the opened state, but can require a greater load to move beyond that point where the slots 49 have closed together. Thus, the petal 44 is less likely to overbend or flip out of position. Another advantage is that this embodiment can be easily adapted to a variety of flexibility configurations depending on the desired attributes. For example the number, sizing, and spacing of the slots 49 can be varied to adjust the amount of allowable bending and the load required to achieve that bend. As with the previously described embodiments, the component or petal 44 can be heat-set to the opened position so that it self-expands from a closed position.

Figure 24:
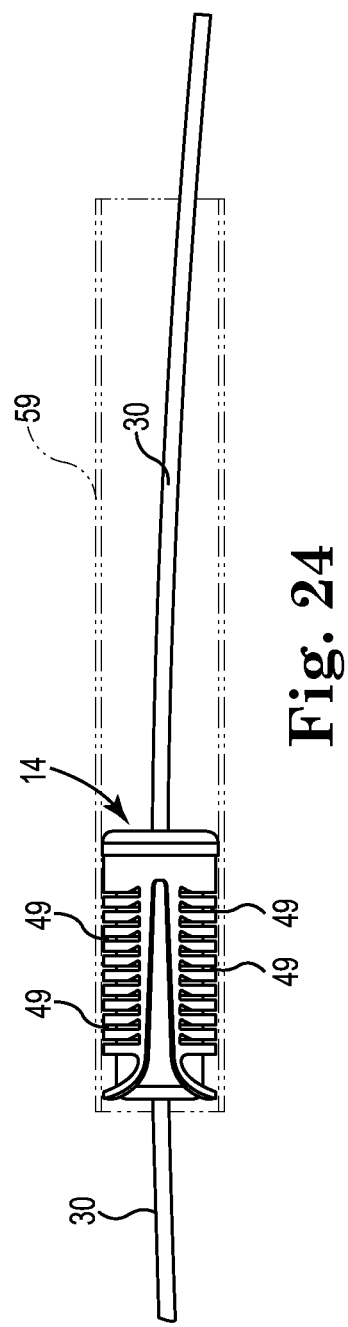
FIG. 24 is a side schematic view of a medial anchor and suture within a delivery tube or oversleeve, in accordance with embodiments of the present invention.
Figure 25:
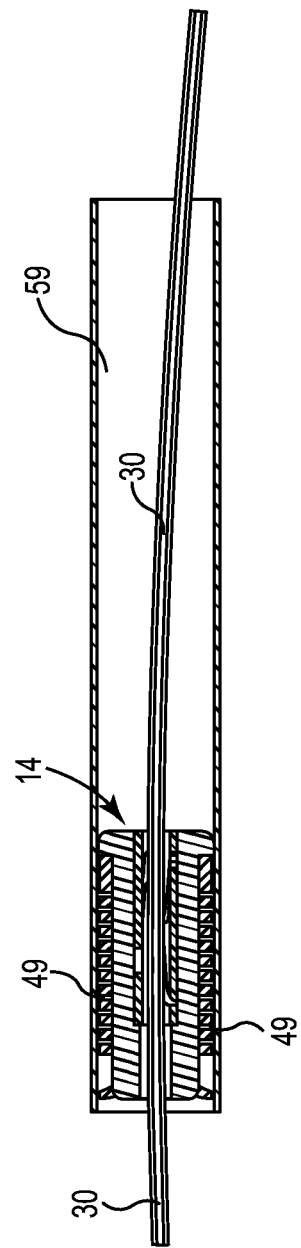
FIG. 25 is a sectional schematic view of a medial anchor and suture within a delivery tube or oversleeve, in accordance with embodiments of the present invention.

Embodiments of the medial anchor 14 can include a body portion 47 and one or more apertures therethrough to receive or connect with the suture 30. Further, a medial needle device or oversleeve 59 can be included with embodiments of the invention to facilitate introduction and deployment of the medial anchor 14. FIGS. 24-25 show the anchor 14 in a contracted state within the lumen of the needle 59 during deployment, with FIGS. 26-27 showing the anchor 14 expanding when pushed, pulled or otherwise removed from the inner constraints of the needle 59. Exemplary anchors 14 can include substances, such as an adhesive (e.g., light activated adhesive) to assist in the tissue engagement process.

Figure 28:
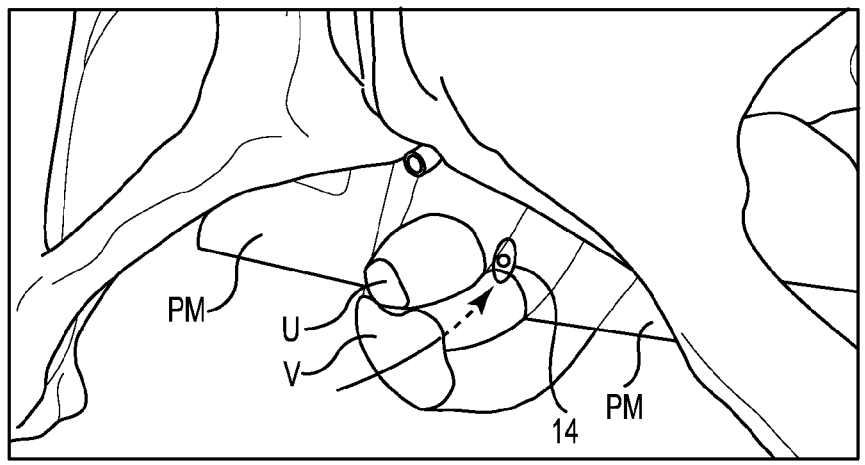
FIGS. 28-30 are schematic views of various anatomical structures of the female pelvic region, and an implant system having medial and lateral anchors, and the deployment method, in accordance with embodiments of the present invention.
Figure 29:
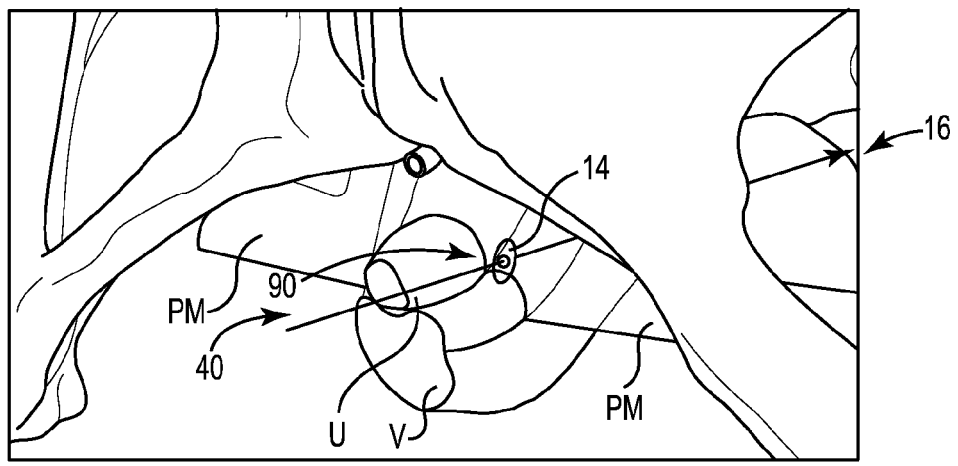
Figure 30:
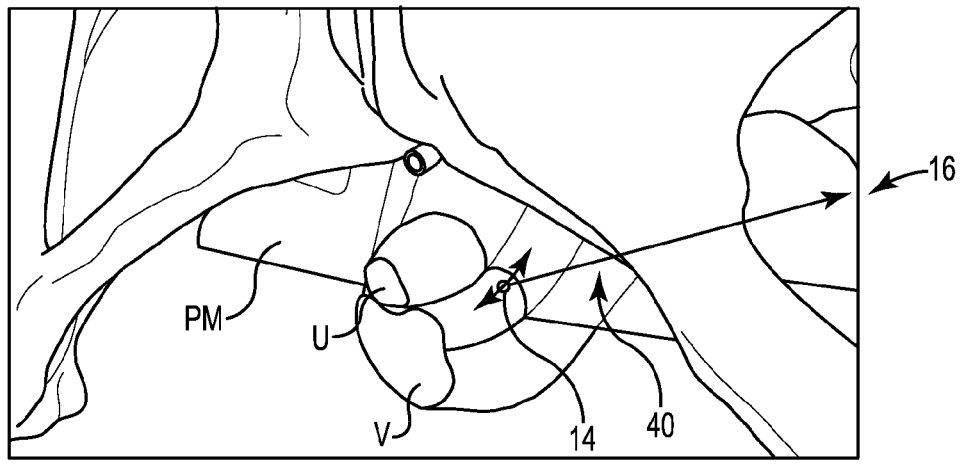
Figure 31:
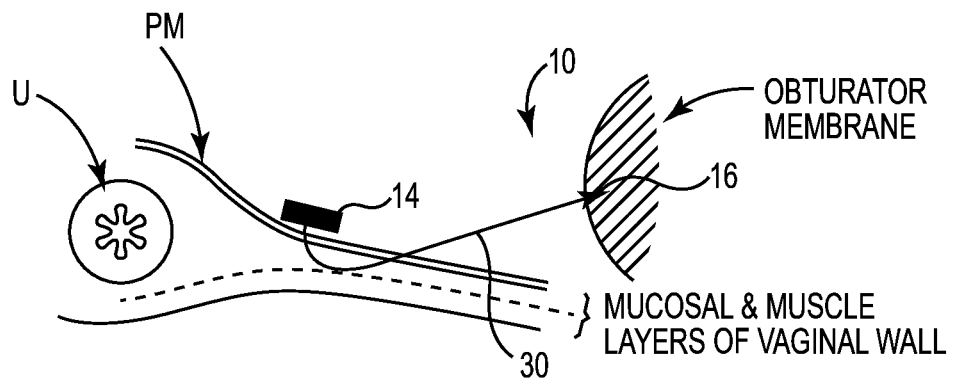
FIGS. 31-38 are schematic views of paraurethral implant systems and methods, with a suture or extension member interwoven or thread through tissue, in accordance with embodiments of the present invention.
Figure 32:
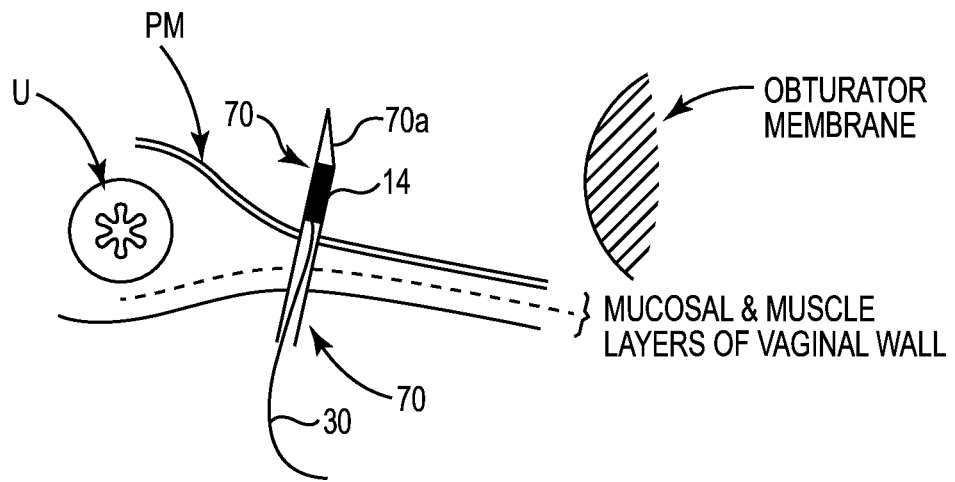
Figure 33:
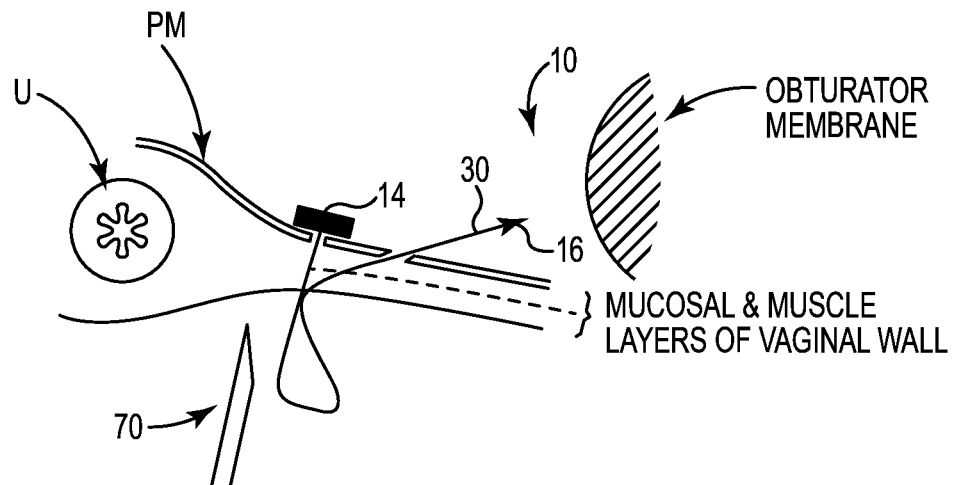
Figure 34:
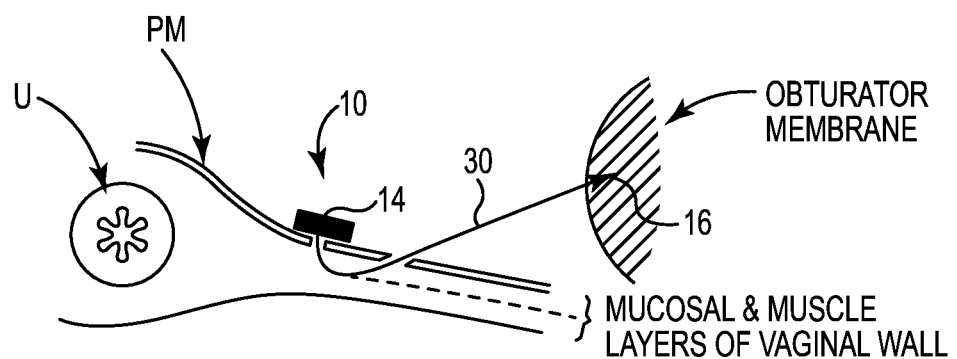

FIGS. 28-30 depicts a medial anchor 14 at the perineal membrane PM implanted via a transverse insertion through the anterior vaginal wall, between the perineal membrane PM and the superficial skin lateral to the urethral meatus, according to an embodiment of the implant 10. While the anchor 14 is held in this position, a needle 40 pass is made from the lateral side of the meatus that intercepts the medial anchor 14 and passes through a pre-made hole or punctures the anchor 14. The needle 40 pass continues on to the obturator muscle, or other distal tissue, where the lateral anchor 16, or anchor array 16n, is delivered. The medial anchor 14 can be placed in the superficial space between the perineal membrane PM and the distal skin layer at the meatus. The small medial anchor 14 can be held with a custom holder or forceps until the intersecting needle 40 pass.

Referring generally to FIGS. 29-30, while the anchor 14 is held, the needle 40 passes through the hole in the anchor 14 and after the distal anchor 16 is deployed and the needle 40 has been retracted, there will be a trailing suture 30 that can include a one-way slider 90, or like sliding or locking device, on it. The slider 90 can be pushed along the suture 30, mating with the anchor 14. Tension is increased by pushing the slider 90 farther along the suture, thereby pressing tighter against the anchor 14, and/or the surrounding tissue. An advantage to this approach is that the placement of the medial anchor 14 at the perineal membrane can be greatly controlled, and can be deployed with minimal disruption to the surrounding tissue.

In contrast, an anchor 14 that is passed through a skin puncture lateral to the meatus may need to be turned such that its major axis is parallel to the puncture hole, then rotated or expanded to face the perineal membrane. The medial anchor 10 for this transvaginal method generally would not have the same size or orientation limits and could therefore be substantially larger and better able to resist pull-through failure.

Furthermore, the medial anchor 14 position could in fact be in the anterior wall of the vagina V for any of the disclosed treatment and anchoring embodiments. Unlike the previous attempts that focused on the anterior vagina, the traction force vector will be more parallel to the vaginal wall with the disclosed embodiments of the present invention so that an optimal rotational resistance of the urethra U can be achieved.

The anchor 14 can be implanted via a puncture at the skin surface, but the introducer needle 40 can still be passed within the thickness of the vaginal wall as described. The anchor 14 can be constructed of a flexible material to reduce the sensation or recognition of the anchor 14 to the patient or the patient's sexual partner. Furthermore, while the anchor 14 is under tension it can bend such that the line of force is generally more parallel to the suture (e.g., reducing the "cheese-cutter" effect). Alternatively, the two ends of the medial anchor 14 can be relatively rigid but flexible in a middle body portion, such that the urethral kinking effect is enhanced when there is tension (e.g., if the flex is near the perineal membrane).

The support or extension members 30 can apply mechanical traction to the urethra in a manner similar to a mini-sling device. However, a benefit of embodiments of the present invention is that the transvaginal placement of the structures and devices does not leave exposed material (e.g., implant mesh) inside the vaginal cavity. For example, the implanted device 10 position is generally blind and lies beyond the superficial mucosal layer of the vaginal wall. Reducing or eliminating the exposed material minimizes the risk of infection, irritation at the surface of the vaginal wall, and provides cosmetic improvement and reduces interference with sexual activity.

As shown in FIGS. 31-38, various embodiments of the implant system 10 can include anchoring elements or portion is fixed on each side of the urethra, on the far side of a tissue layer that is known to have relatively high strength and toughness. The medial or proximal anchor 14 can include a "toggle" anchor, which is a small, elongated structure that can be placed through a small puncture or like incision and then rotates after deployment so that it cannot back out through the incision hole. Other anchoring devices and methods can be employed with the present invention as well.

As shown with various embodiments, the suture 30 can weave or thread in and out of, and along, the tissue, e.g., the perineal membrane, to provide a supportive undulating layout for the suture 30 and implant 14 combination. This can facilitate attachment, better distribute pulling force on or along the tissue, and provide like support benefits. For instance, one or more sutures 30 can be woven or interwoven (e.g., in and out) of the perineal membrane, with anchors 14 engaging at or proximate the posterior symphysis. When tightened, the suture 30 pulls and compresses tissue toward the posterior symphysis to provide support and strength. Again, a suture lock device or technique can be included to fix the tension or support adjustment of the sutures 30.

Placing the anchor device 14 on the far side of the fascia is advantageous because it is less likely to be palpable than one placed in the mucosal and muscle layer—also because it is placed in an area of loose connective tissue in which the toggle anchor 14 can easily rotate into a locking orientation.

The distal or anchor device 16 is placed in a lateral or superior position such that a connection (e.g., suture 30 or wire connection) between the medial and lateral anchors 14, 16 can provide tensile support for the urethra during stress events. The anchor device 16 can be fixated to, or engaged with, the obturator membrane, obturator internus, tendinous arch of the levator ani (white line), the Cooper's ligament, sacrospinous ligament, prepubic fascia or muscle, the pubic symphysis cartilage, abdominal fascia, or other stable anatomical features.

The final position of the implanted device 10 creates a support structure that is similar to a needle suspension. The medial anchor 14 can spread or better distribute the tension load over a larger surface (as opposed to a thin suture cutting edge surface) than other procedures and devices. This, in turn, promotes stability of the anchor and connecting suture or spanning support member.

Various procedural steps or methods can be employed to deploy the implant 10 of the present invention. In one embodiment, as demonstrated with FIGS. 31-35, the medial toggle anchor 14 is implanted, a needle 70 is withdrawn, a free suture or connector end is delivered through the insertion opening, the lateral (e.g., obturator) anchor 16 is delivered and implanted, and the connecting suture 30 is properly tensioned between the anchors 14, 16 to provide proper support.

Figure 35:
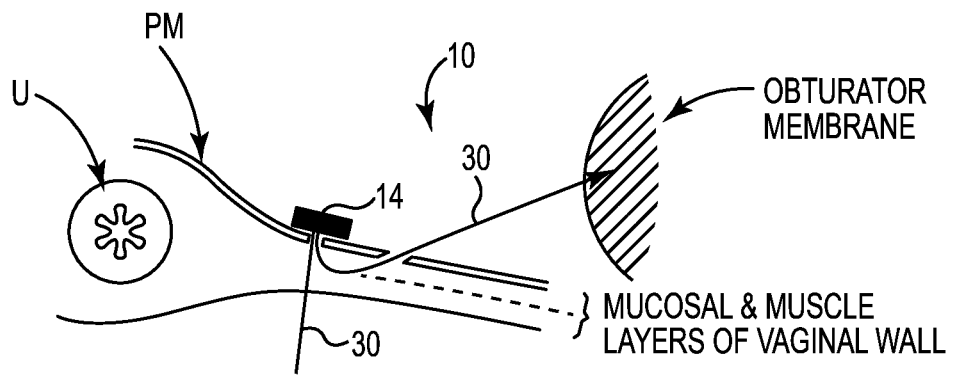

The needle 70 can be adapted to contain the toggle anchor 14 with a tip 70a directed for penetration through the perineal membrane or like paraurethral support tissue. In other embodiments, the toggle anchor 14 can include a sharp or beveled tip to facilitate penetrating through the target tissue. The needle 70 is then withdrawn with the suture 30 extending therefrom and a distal anchor 16 attached or provided at the opposing free end of the suture 30. The anchor 16 can be small enough to pass through the small punctures in the tissue and deploy at the obturator foramen or like tissue targets. Various delivery tools and devices disclosed herein, or known, can be used to direct and deploy the anchor 16. Upon implantation of the anchor 16, the suture 30 can be tensioned to provide the desired level of support for the paraurethral tissue (FIG. 35). In addition, the medial anchor 14 can include a one-way tension holding feature (e.g., zip tie-like) that allows the physician to pull out excess suture material without the excess slipping back through the anchor 14.

Figure 36:
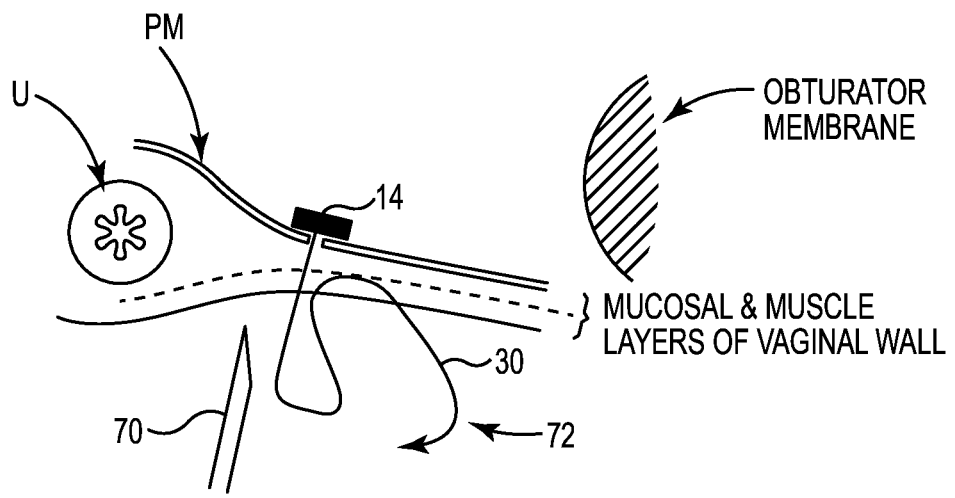
Figure 37:
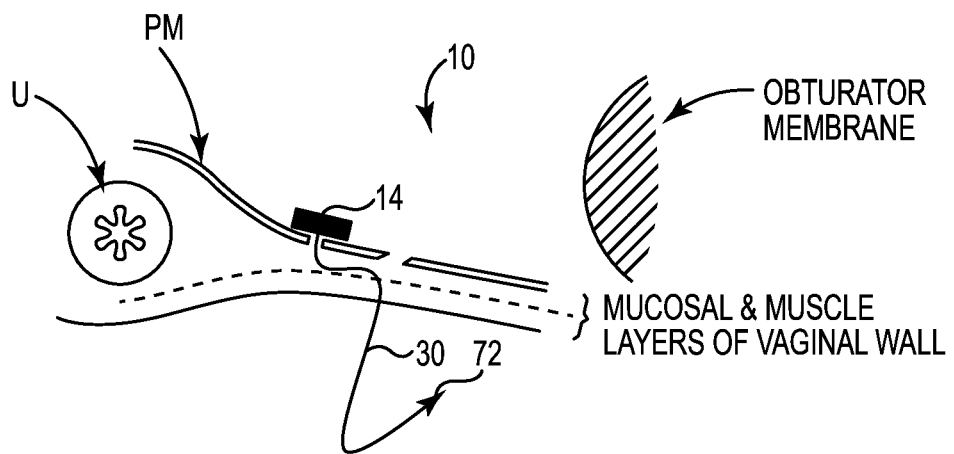
Figure 38:
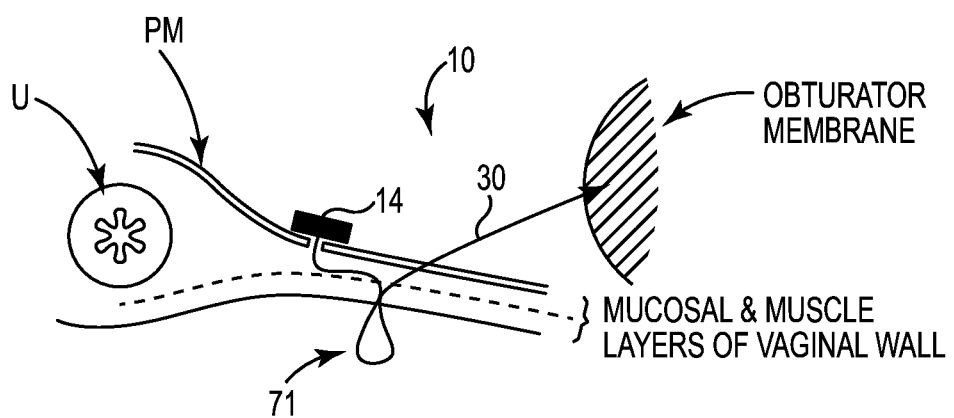

FIGS. 36-38 show another embodiment of the implant 10 having a toggle anchor configuration. A suture needle 72 can be utilized to create a loop or "bite" 71 through the paraurethral tissue to provide additional stability and anchoring support. The suture needle 72 can be included with the suture 30, and can be removable with certain embodiments.

Figure 68:
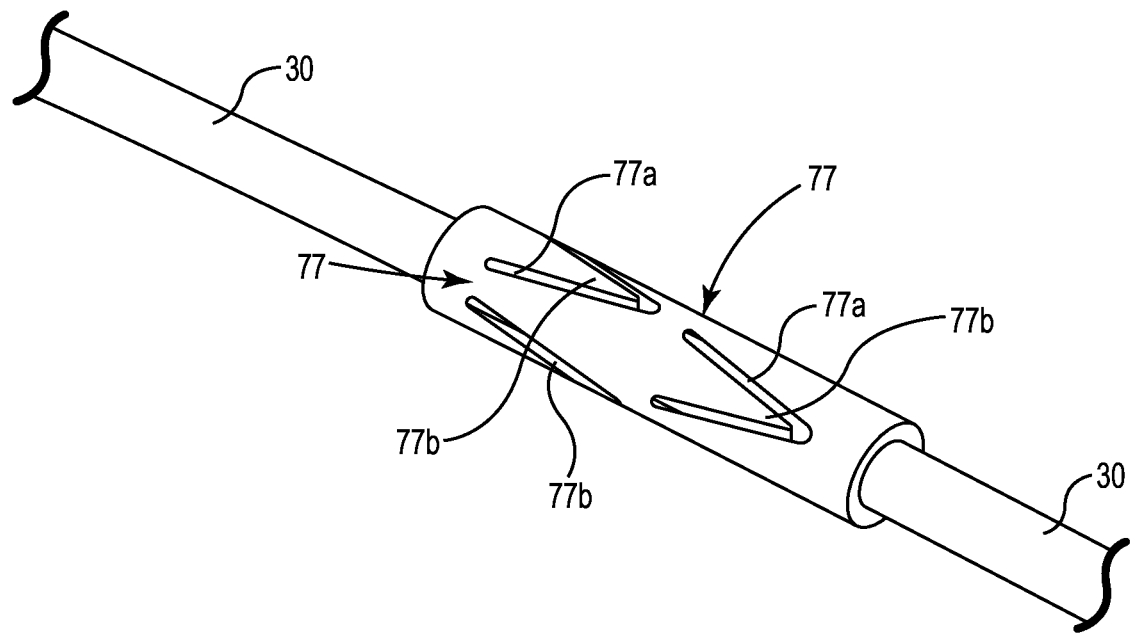
FIG. 68 is a schematic view of a suture locking device for use with embodiments of the present invention.

In various embodiments, the suture 30 can be woven in and out of multiple portions of the perineal membrane or like tissue, with or without a medial anchor 14, such that pulling on the suture 30 can compress or cinch up the tissue. One or more suture locking devices 77, e.g., diametric suture lock of FIG. 68, can be inserted through a portion (e.g., free end) of the suture 30 to selectively lock the suture in place after the desired tension is obtained. In certain embodiments, the suture locking devices 77 can include a one-way locking mechanism constructed of a generally cylindrical body having one or more cuts 77a (e.g., laser cut) defined in a surface or portion of the device 77 to define inward extending tines 77b. The tines 77b can permit the suture 30 to ride or slide within the device 77 in a direction not against the direction of the tine 77b angles. However, backing out of the suture 30 will be prevented in the opposite direction when the tines 77b grab onto the suture (e.g., braided suture) and restrict movement in that direction. Other suture locking devices are envisioned for use with various embodiments of the present invention as well.

Figure 39:
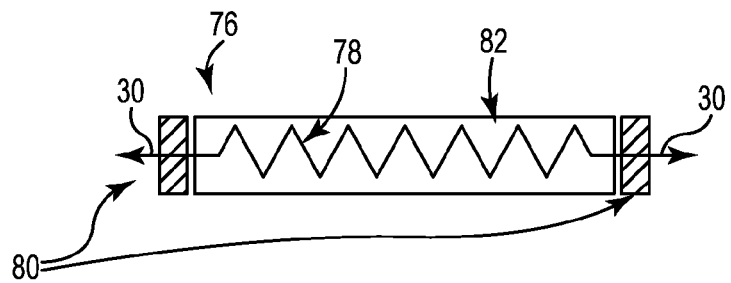
FIG. 39 is a schematic view of a coil spring device operably connected to one or more anchors for use in an implant system and method in accordance with embodiments of the present invention.

As illustrated in FIG. 39, embodiments of the present invention can include a coil spring device 76 operably connected to one or more of the anchors 14, 16. The device 76 can be held in a slightly extended state that generates a preload tension. The device 76 can include a spring mechanism 78, which is connected at either end to the suture 30 and is forced open with stops 80 that impose a fixed extension against a rigid structure or housing 82. Thus the spring 78 may extend, but only after the suture tension exceeds the preload force. Alternatively, a conventional coil extension spring can be employed such that when the spring relaxes to its solid height, some pretensioning load is maintained—e.g., it is unable to further contract due to the coils being in full contact. Other methods for mechanically creating initial tension and load control are envisioned as well.

In certain circumstances, it may be desirous to provide pre-loaded tension options for one or more of the anchors 14, 16. Preloading can be achieved by pretensioning the suture during the implantation procedure or could be achieved by creating mechanical pretension internally in the anchor devices 14, 16, or mechanisms operably connected to the devices 14, 16. As such, a constant rest load against tissue (which might stretch) can be provided.

Figure 40:
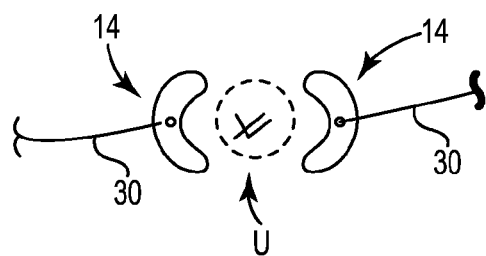
FIG. 40 is a schematic view of tissue engagement devices for a medial anchor, in accordance with embodiments of the present invention.

As shown in FIG. 40, embodiments of can include one or more generally C-shaped, or like shaped, medial anchors 14. The anchors 14 can be placed adjacent the urethra U to provide a medial anchor configuration. The sutures 30 can extend from the anchors 14 to one or more distal anchors 16.

Certain embodiments of the anchors 14, or 16, can include space-expanding characteristics or attributes. A expandable portion anchors 14, 16 can be constructed of shape memory materials (e.g., polymers or metals) adapted to collapse under a bias within a delivery tool or under other pressure, with the anchors 14, 16 expandable upon deployment to provide traction-like fixation or connectivity to tissue.

Figure 41:
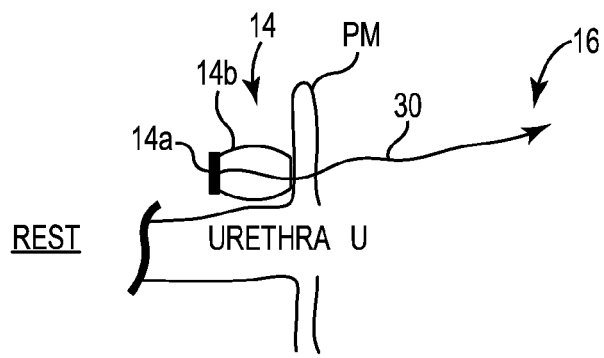
FIGS. 41-42 are schematic views of a dilating medial anchor device in accordance with embodiments of the present invention.
Figure 42:
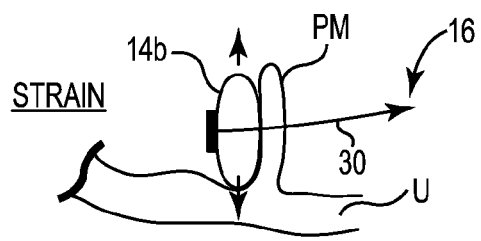
Figure 48:
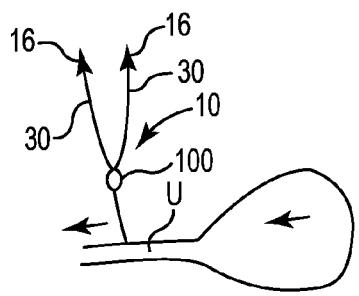
FIGS. 48-54 are schematic views of a suture and cinch device implant, in accordance with embodiments of the present invention.
Figure 49:
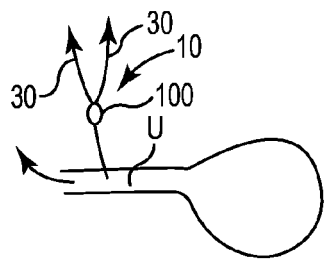

FIGS. 41-42 show an embodiment of the medial anchor device 14 having an anchor base portion 14a and a dilating anchor portion 14b. The dilating anchor portion 14b is adapted for deployment to rest or otherwise stop or abut against a portion of the perineal membrane PM, or other like tissue. The suture or other extension member 30 can extend between the two anchors 14, 16. In a rest state (FIG. 41), the dilating anchor portion 14b is not generally applying pressure to the urethra U. However, during a straining event or state, the dilating anchor portion 14b expands (e.g., expands under compression) to apply a level of pressure on the urethra U to promote continence, as depicted in FIG. 42.

FIGS. 43-45 are directed to a medial anchor device adapted to puncture through the skin and into the perineal membrane PM or like tissue. Such a superficial skin puncture can be targeted at the crease between the labia minora and majus, directed at the space between the bulb of vestibule and clitoral crus, in certain embodiments. A tube or delivery needle 84 can include or contain a pair of anchoring or stop members 86a, 86b and at least a portion of the member 30. The needle 84 operably connects or carries the stop members 86a, 86b and extends beyond them. Upon insertion into the perineal membrane, as shown in 44, the delivery needle 84 can be removed, leaving behind the stop members 86a, 86b and the member 30, such as a suture, with a stop member on each side of the perineal membrane PM. The members 86a, 86b can then be drawn to compress or otherwise secure the stop members on each side of the membrane, as shown in FIG. 45. A knot or other device 87 or technique can be created or provided along a portion of the member 30, e.g., on each side of the stop members 86a, 86b, to secure the members in place. As an alternative to a knot, a clip, tie, washer, lock mechanism or other devices and techniques can be employed to secure the stop members 86a, 86b in place against the perineal membrane. Once implanted and adjusted, the device can provide tension and a twisting motion on the membrane, thereby translating to rotational torque. Again, the free end of the extension member 30 can include one or more lateral anchor devices 16 as disclosed herein.

FIGS. 46-47 show a medial anchor device 14 having a generally star-shaped construct. The device 14 is collapsible and expandable to facilitate introduction and deployment. The anchor 14 can be constructed of a shape memory material such that it can be implanted in a collapsed state (FIG. 47) and expands once through the tissue to provide desired engagement (FIG. 46). Various metal or polymer materials can be used to construct such an anchor 14 to adjust tensioning and tissue positioning at the perineal membrane to promote continence. Other selective expansion anchor devices can be employed as well, including anchors constructed of an expandable balloon or bladder-like material, adapted to expand within a tissue or compartment. Other anchors can include threading or drill-like configurations for engaging and anchoring into tissue such as the perineal membrane PM. Twisting or rotating motion of the anchor at the target tissue site (e.g., electric, mechanical or manual), can facilitate penetration and affixation of the anchors with the perineal membrane PM.

Certain embodiments of the medial anchor 14 can include structures adapted to attach to or span across a portion of the perineal membrane, or like tissue, to facilitate engagement, compression or anchoring with the tissue. For instance, a plate, mesh material, tissue cinching device, stent-like device, ring, clip, coil, spring, strap, pad, patches, or similar structures, can be affixed to, directly or indirectly, the perineal membrane, with such anchors 14 then being connected to the lateral anchor 16 via the extension member 30. These structures can be attached to tissue via sutures, anchors, and similar tissue engagement devices. The anchors 14 and related structures can include rigid, semi-rigid or flexible polymer or metal materials.

One-way locking devices can be incorporated with any of the anchors 14, 16, or along (e.g., thread along) the member 30 such that the physician can adjust the tensioning of the implant 10 to the desired level and fix the tension for optimal support and the promotion of continence.

In use, a patient could be placed in a lithotomy position for the implantation procedure. A physician may make one or more incisions through the perineal tissue lateral to the urethra of the patient. Alternatively, the physician may make one or more vaginal incisions to access the tissue superior to the urethra. The physician may use the needle delivery device 40 to implant the devices or anchors. The medial or proximal anchor 14 can then be implanted through the perineal incision, thereby reducing the invasiveness of the procedure. The delivery device 40 may be configured to allow insertion through a single or multiple perineal or transvaginal incisions. In other embodiments of the implant treatment procedure, needle 40 can be directed "outside-in," from the skin through the obturator membrane, then with an anchor 14 engaged with the perineal membrane. Further, the anchor 14 can include suture loops. The loops can be tied from the peritoneum side. From the obturator side, the multiple loops or sutures 30 can then be tied around the anchor for fixation.

In other embodiments, the distal anchor 16 is a wrap-around device adapted to go around the inferior ramus. This, in turn, can reduce or eliminate the chance of pull-out from soft tissue. Sutures, clips, clamps, loops and like devices can be employed to facilitate and affix the wrap-around configuration. Certain embodiments can use distal anchors, such as anchors 16, to attach to the retropubic space of the patient as well, with the attached suture 30 again extending to the medial anchor 14 at the perineal membrane.

The implant 10, or corresponding anchors, can benefit from a wound healing response that restores or even improves tissue strength. However, such healing and tissue reinforcement can take several weeks. As such, one solution to this problem is to implant the anchor 14 or graft several weeks prior to implantation of the tensioning sutures and anchors 16, 16n. The anchor 14 can be embedded or engaged at the perineal membrane with a minor procedure and allowed to fully heal and integrate with the surrounding tissue for a period of days or weeks. Because there is no active loading on the anchor 14 during this period, the patient can maintain full physical activity levels during this healing process. Then, in a follow-up visit, a minimal procedure is conducted to attach this fully anchored element 14 to the distal anchor 16, or array 16n, via the tensioning suture 30.

In certain embodiments, it may be beneficial to modify the target anchor zone or site (e.g., perineal membrane) through the use of injectables such as a scarring agent, proteins, polymers, or other materials that significantly increase tissue strength in the region. After allowing this treatment to set up, the continence implant 10 can be implanted in a follow-up procedure.

Alternatively, the full implant 10 can be implanted but left in a loosened state with the free end of the suture 30 left hanging or free. After several weeks, the implant 10 can be tightened by pulling the suture 30 (or by adjusting a locking or securement device) further out and then trimming it off.

Below the perineal membrane is the superficial perineal pouch (SPP), which is large enough to accommodate various implants or anchors 14 for embodiments of the present invention. The SPP is the compartment of the perineum that lies between the perineal membrane and the perineal fascia (Colles fascia). The anterior SPP can be dissected from the frontal side in order to expose the tissue in this space. This area generally consists of layers of connective tissue and fascia, and some thin muscle. The tissue in this region is easily penetrated or compressed with a blunt needle, until reaching the perineal membrane. Thus, there can be ample room and favorable tissue properties in this region to accommodate the implant 10 or anchoring devices.

Figure 50:
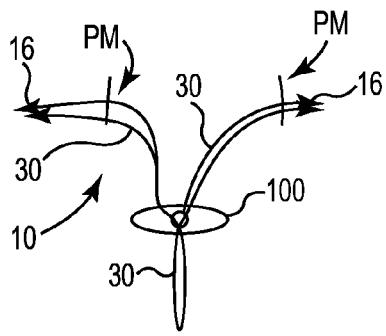
Figure 51:
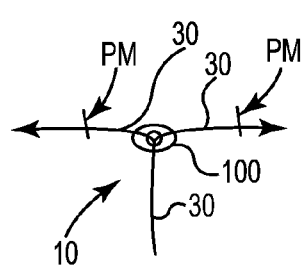
Figure 52:
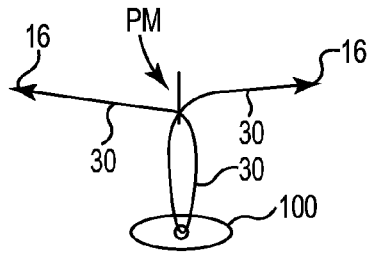
Figure 53:
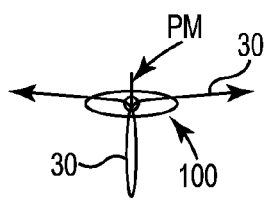
Figure 54:
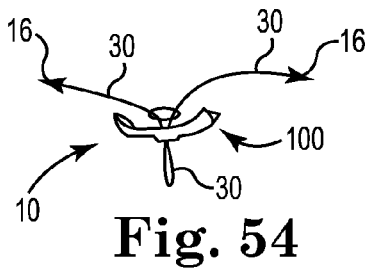

FIGS. 48-54 depict implants 10 adapted for fixation with the perineal membrane to provide adjustment (such as lift), to thereby provide support and adjustment of the patient's urethra U. FIGS. 50-51 show an embodiment having two perineal membrane PM piercing or penetration points, with the implant including a small cinch ring 100 adapted to pull on the members 30 (such as suture, strand, mesh, etc.) to provide the desired adjustment—e.g., along a suture loop. Lateral anchors 16 can be adapted to penetrate through the perineal membrane PM for fixation and securement distal the paraurethral tissue. The cinch ring 100 can slide up to the desired position along the members 30 to provide selective adjustment and tensioning, as shown in 51. The ring 100 can include a stop button or collar having a one-way draw string or device to provide securement as well. FIGS. 52-53 show an embodiment of the implant adapted for a single perineal membrane piercing or penetration. Further, FIG. 54 depicts a curved profile for the ring 100 to distribute pressure from the implant 10.

Figure 55:
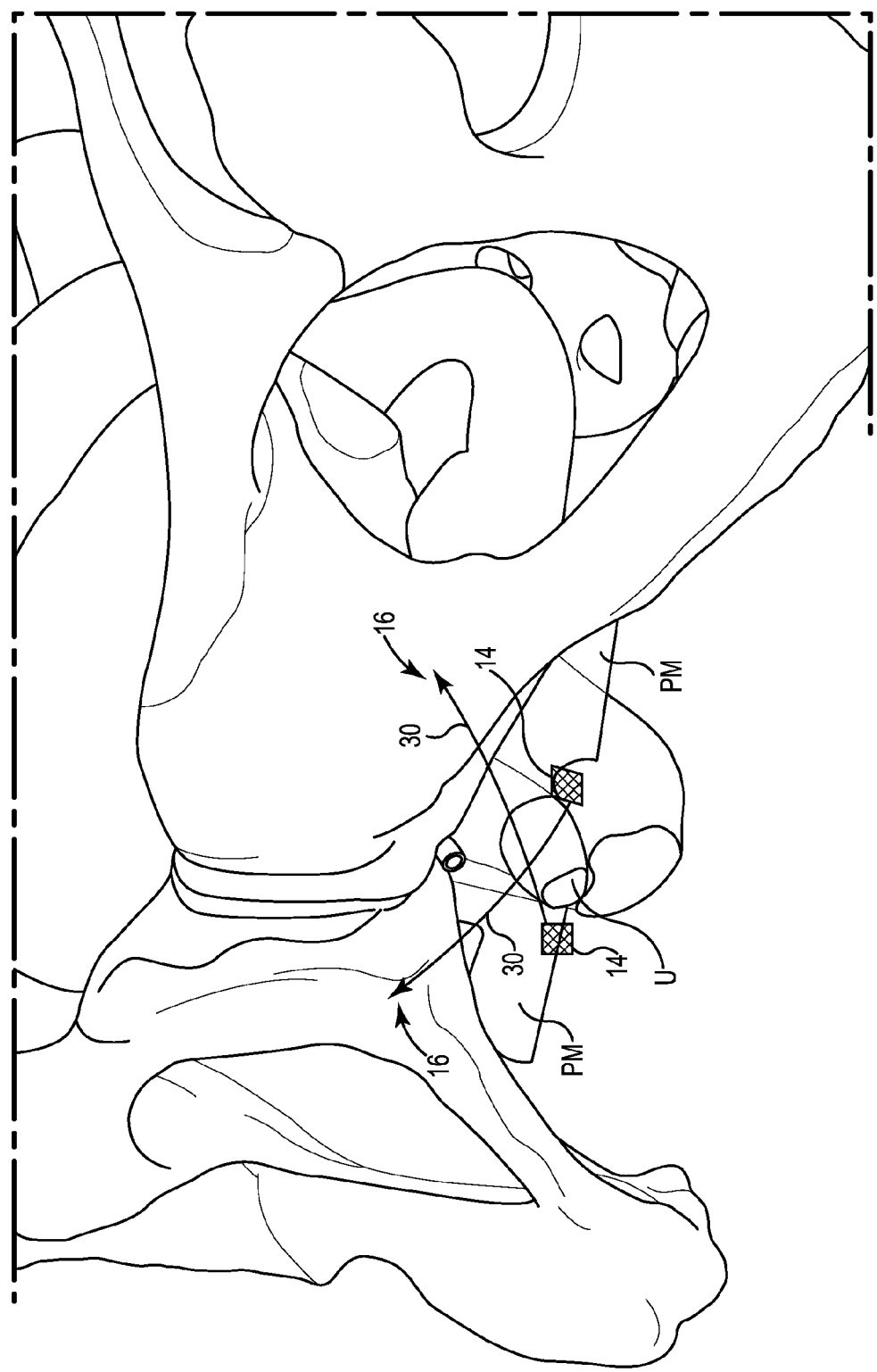
FIG. 55 is a schematic view of various anatomical structures of the female pelvic region, and an implant system having medial anchors, lateral anchors, and crossing extension members, in accordance with embodiments of the present invention.

As shown in FIG. 55, embodiments of the implant system 10 can include members, such as sutures 30, adapted to cross over each other, with distal end anchors 16 fixated in tissue away from the perineal membrane PM. This, in turn, can coapt or compress the urethra while providing tension and desirable support characteristics, while reducing undesirable rotation. Medial anchors 14, such as patches or like anchor structures, can press against, affix or engage the perineal membrane to provide a larger anchoring area.

Figure 56:
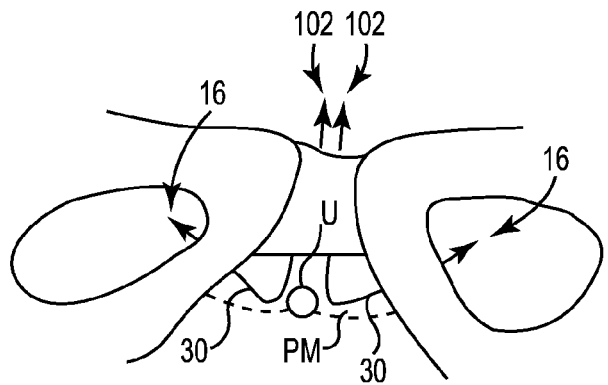
FIG. 56 is a schematic view of an implant system having suture anchors in the perineal membrane, in accordance with embodiments of the present invention.

Certain embodiments, like that shown in FIG. 56, can engage and anchor to the perineal membrane with only sutures 30. Namely, a length of suture 30 is pushed through the tissue (e.g., one on each side of the urethra U in the perineal membrane PM) with an end anchored in the disclosed distal anchor target tissue via anchor 16 (e.g., obturator or like target locations) and another end anchor 102 anchored in other tissue, such as the rectus fascia or like tissue.

Figure 57:
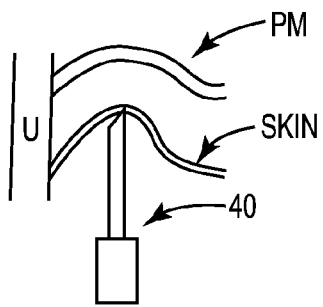
FIG. 57-62 are schematic views of an anchor and needle introduction system for use with embodiments of the present invention.
Figure 58:
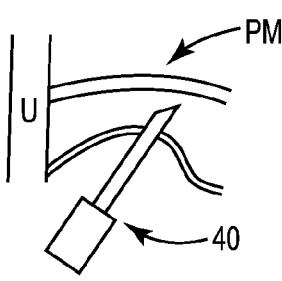
Figure 59:
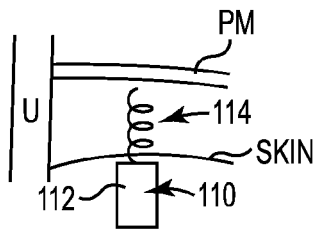
Figure 60:
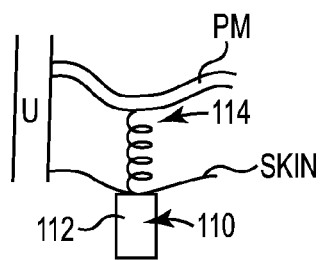
Figure 61:
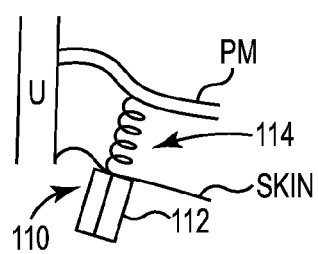

FIGS. 57-62 are directed various embodiments of anchor introduction system 110 for use with embodiments disclosed herein. FIGS. 57-58 show problems with tissue deflection that can occur when the needle 40 punctures the skin, for those embodiments employing percutaneous anchor or implant deployment, as the needle 40 approaches the perineal membrane PM, next to the urethra U. The needle 40 can be undesirably diverted laterally before puncturing the perineal membrane PM. Embodiments of the system 110 are therefore provided to limit the movement of tissue being punctured or traversed by a needle deployment device 40 to ensure that a proper and desirable puncture depth is achieved.

Figure 62:
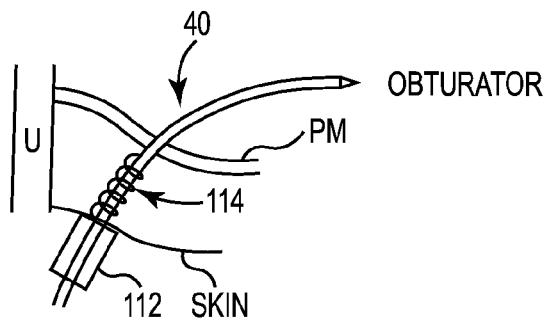
Figure 63:
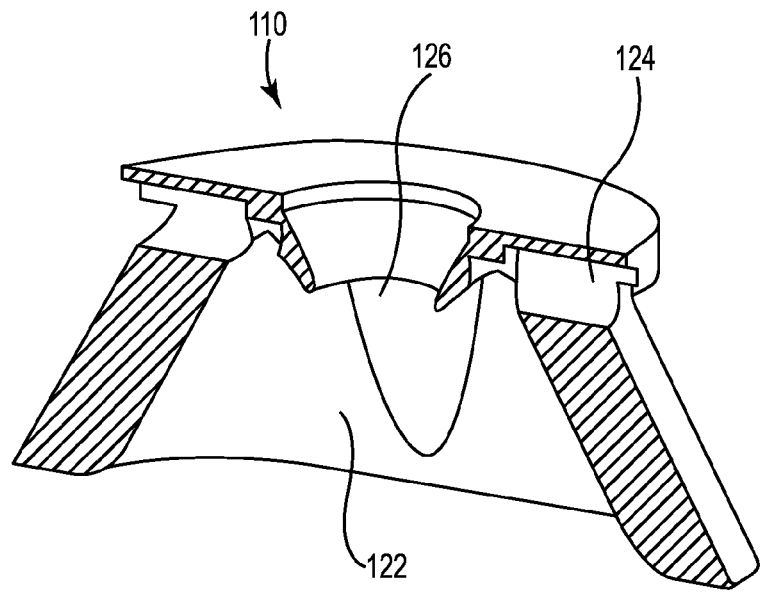
FIGS. 63-67 are partial schematic sectional views of a tissue separation device for use with embodiments of the present invention.

The system 110 can include the needle 112 having a helical or corkscrew-like end member 114. Upon insertion of the member 114 through the skin and toward the perineal membrane PM, the needle path is controlled such that it does not divert laterally. The coil member 114 will engage the perineal membrane PM (FIG. 61) and provide an operative path for the needle device 40 to enter through the skin and through the membrane PM (FIG. 62). In certain embodiments, the member 114 can be constructed of a bioabsorbable material, such as a bioabsorbable polymer, and left behind in the patient. As such, the member 114 can serve as a temporary support for an anchor device 14 inserted via the needle.

As shown in FIGS. 63-67, a tissue separation device 120 can be constructed as a rigid or elastic part that includes a vacuum chamber 122 into which tissue can be drawn, one or more vacuum ports 124 connected to an external vacuum source, and an aperture 126 through which an introduction or delivery device 40 can pass.

The device 120 can be particularly useful in creating appropriate needle pathways for minimally invasive (percutaneous) insertion of implants or anchors. The traction provided by the vacuum also serves to hold the tissue stationary so that minimal "tenting" or displacement of the tissue occurs during the needle penetration.

The tissue separation device 120 includes features specifically directed to creating separation of tissue layers. The aperture 126 can be surrounded by a perimeter configuration that is angled down and adapted to contact tissue to form an interior vacuum seal. The perimeter can be constructed of a rigid or elastic material that is suitable for forming a good seal against tissue, such as the perineal membrane or the vaginal mucosal layer.

Figure 64:
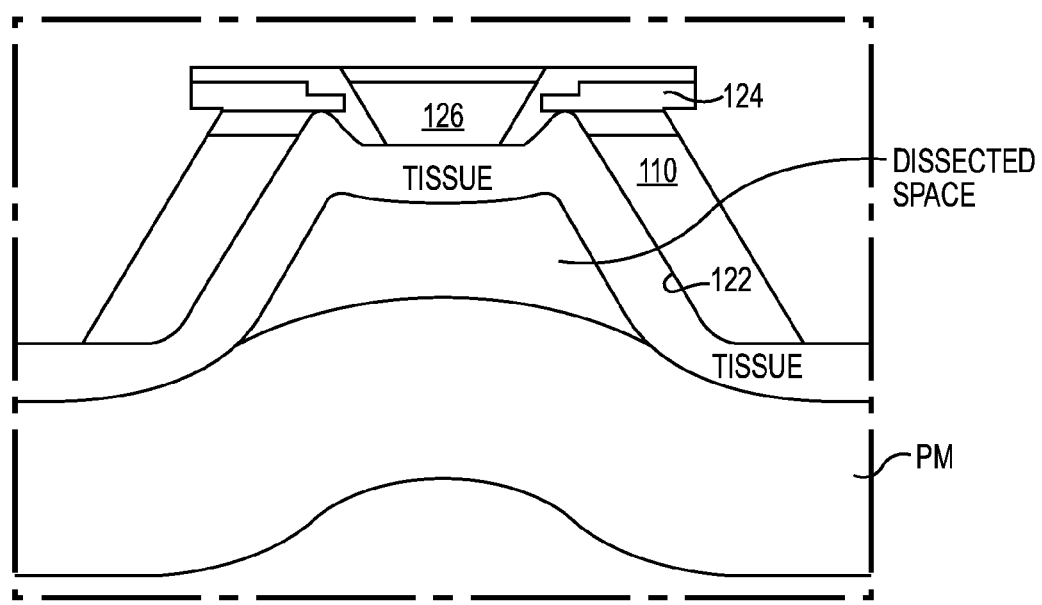

As shown in FIG. 64, the interior geometry of the device 120 is sized and shaped such that only the thin tissue layer is drawn into the cup space. The tissue wall is drawn in because it is more elastic and is thin enough to fold into the space. For vaginal wall traction, the underlying muscularis is too thick and stiff to fit into the space. As such, a separation of the tissue layers is created.

Figure 65:
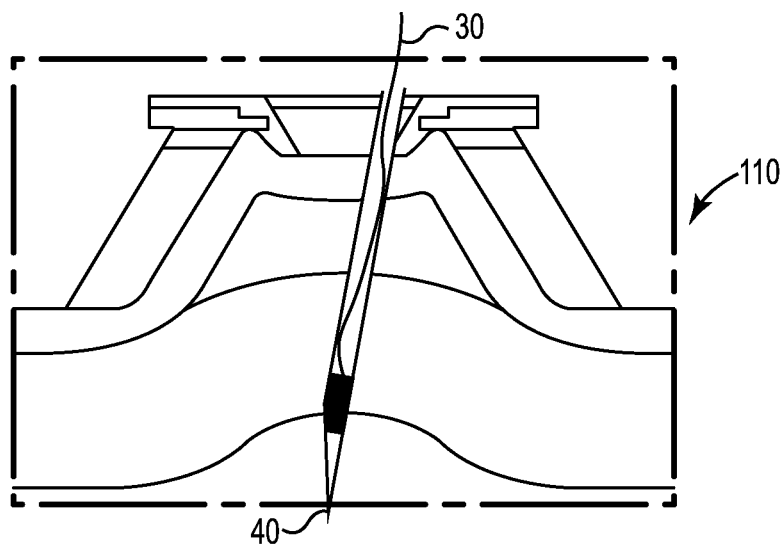
Figure 66:
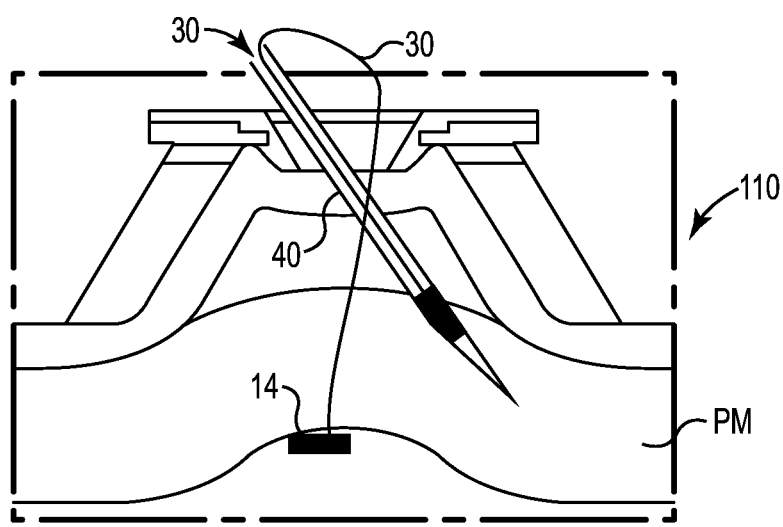
Figure 67:
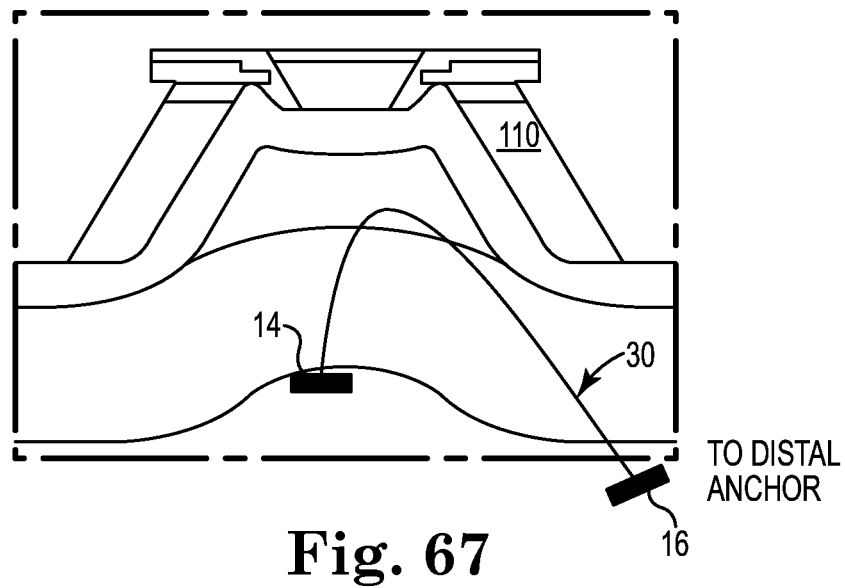

A first anchor (e.g., toggle) 14 of an implant device 10, as shown in FIGS. 65-66, can be introduced through the aperture 126 that penetrates through the mucosal or other tissue layers, leaving the anchor 14 deployed on the opposite side of the tissue. After the first anchor 14 of the implant is deposited or fixated, the needle 40 can be partially withdrawn into the dissected space and redirected toward the distal or lateral anchor target (e.g., via anchor 16, or anchor array 16*n*).

For those embodiments including one or more needles 40 to introduce and deploy anchors for tissue engagement, a trocar slidably housed within the needle to control and facilitate tissue traversal and piercing or penetration at the target site.

The systems, devices, configurations and methods disclosed herein have generally described anchors that are symmetrically, bilaterally, positioned about the urethra. However, a single side deployment configuration can still achieve continence and is available with various embodiments. For instance, a single medial anchor 14 and lateral anchor 16, or lateral anchor array 16*n*, can be connected by a suture 30 to support and adjust the perineal membrane, above, below, or on a side of the urethra.

The systems, their various components, structures, features, materials and methods of the present invention may have a number of suitable configurations as shown above. Various methods and tools for introducing, deploying, anchoring and manipulating implants or to treat incontinence and prolapse as disclosed in the previously-incorporated references are envisioned for use with the present invention as well.

A variety of materials may be used to form portions or components of the implants and devices, including Nitinol, polymers, elastomers, porous mesh, thermoplastic elastomers, metals, ceramics, springs, wires, plastic tubing, and the like. The systems, components and methods may have a number of suitable configurations known to one of ordinary skill in the art after reviewing the disclosure provided herein.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A system for treating incontinence in a patient, comprising:
   a first implant device having at least one non-mesh first medial anchor, a first distal anchor, and a first extension member operably connecting the at least one first medial anchor and the first distal anchor, the first medial anchor having an extendable transverse extension portion adapted to engage a portion of the perineal membrane to provide support for the urethra to restore continence; and
   a second implant device separate and not physically connected, directly or indirectly, with the first implant device and having at least one non-mesh second medial anchor, a second distal anchor, and a second extension member operably connecting the second medial anchor and the second distal anchor, the second medial anchor having an extendable transverse extension portion adapted to engage a portion of the perineal membrane, separate from the portion of the perineal membrane, and at an opposing side of the urethra, engaged by the at least one first medial anchor, to assist in supporting the urethra to restore continence, and wherein the separated first and second implant devices together form a general V-shaped support configuration relative to the perineal membrane.

2. The system of claim 1, wherein the first extension member includes a suture.

3. The system of claim 1, wherein the first extension member is selected from a group consisting of: a braided member, an elongated mesh, a flexible rod, a rigid rod and a length-adjustable member.

4. The system of claim 1, wherein the first distal anchor includes a first array of anchors, each of the first array of anchors having expandable barbs and being operably connected to the first extension member.

5. The system of claim 4, further including an introduction needle having a lumen extending therethrough, wherein at least the first array of anchors are adapted to traverse the lumen in a compressed state.

6. The system of claim 1, wherein the second distal anchor includes a second array of anchors, each of the second array of anchors having expandable barbs and being operably connected to the second extension member.

7. The system of claim 1, wherein the at least one first medial anchor includes one or more expandable fins adapted for engagement with the portion of the perineal membrane.

8. The system of claim 1, wherein at least the second medial anchor includes expandable fins adapted to engage the second medial anchor device to the portion of the perineal membrane separate from the portion of the perineal membrane engaged by the at least one first medial anchor.

9. The system of claim 1, wherein the portion of the perineal membrane engaged by the at least one first medial anchor is on a side of the urethra.

10. The system of claim 1, wherein the portion of the perineal membrane engaged by the at least one first medial anchor is generally above the urethra.

11. The system of claim 1, wherein the portion of the perineal membrane engaged by the at least one first medial anchor is generally below the urethra.

12. The system of claim 1, wherein the first distal anchor is adapted to engage a target tissue site selected from the group consisting of: the obturator foramen, obturator internus, abdominal fascia, sacrospinous ligament, prepubic fascia, rectus fascia, the tendinous arch of the levator ani, the Cooper's ligament, and the pubic symphysis cartilage.

13. The system of claim 1, wherein the at least one first medial anchor or the first distal anchor include an adhesive to assist in tissue engagement.

14. The system of claim 13, wherein the adhesive is a light-activated adhesive.

15. A system for treating incontinence in a patient, comprising:
a first implant device having a non-mesh first medial anchor and a first extension member, the first medial anchor having a pivotable radial extension portion adapted to affix to a portion of the perineal membrane of the patient on a first side of the urethra;
a second implant device separate and unconnected from, directly or indirectly, the first implant device and having a non-mesh second medial anchor and a second extension member, the second medial anchor having a pivotable radial extension portion adapted to affix to a portion of the perineal membrane of the patient on a second side of the urethra opposite the first side of the urethra, such that the separated first and second implant devices together form a general V-shaped support configuration relative to the perineal membrane; and
wherein tensioning adjustment on at least the first implant device provides support for the urethra to restore continence.

16. The system of claim 15, wherein tensioning adjustment on the first implant device and the second implant device provides support for the urethra to restore continence.

17. The system of claim 15, wherein at least one of the first extension member and the second extension member includes a suture.

18. The system of claim 15, wherein at least one of the first extension member and the second extension member includes an elongate mesh.

19. The system of claim 15, further including a first distal anchor device operably connected to the first medial anchor via the first extension member.

20. The system of claim 19, wherein the first distal anchor device includes a first array of anchors, each of the first array of anchors having expandable barbs and being operably connected to the first extension member.

21. The system of claim 20, further including an introduction needle having a lumen extending therethrough, wherein at least the first array of anchors are adapted to traverse the lumen in a compressed state.

22. The system of claim 19, wherein the first distal anchor is adapted to engage a target tissue site selected from the group consisting of: the obturator foramen, abdominal fascia, rectus fascia, the tendinous arch of the levator ani, the Cooper's ligament, and the pubic symphysis cartilage.

23. The system of claim 15, further including a second distal anchor device operably connected to the second medial anchor via the second extension member.

24. The system of claim 23, wherein the second distal anchor device includes a second array of anchors, each of the second array of anchors having expandable barbs and being operably connected to the second extension member.

25. The system of claim 15, wherein at least the first medial anchor device includes expandable fins adapted to affix the first medial anchor device to the portion of the perineal membrane.

26. The system of claim 15, further including an introduction needle having a lumen extending therethrough.

27. A system for treating incontinence in a patient, comprising:
a first implant device having a non-mesh first medial anchor device, a first distal anchor device, and a first extension member operably extending between the first medial anchor device and the first distal anchor device, the first medial anchor device having one or more member portions extendable out radially therefrom and adapted to affix to a portion of the perineal membrane of the patient on a first side of the urethra and the distal anchor device adapted to affix to tissue away from the perineal membrane;
a second implant device physically separate and unconnected, directly or indirectly, with the first implant device and having a non-mesh second medial anchor device, a second distal anchor device, and a second extension member operably extending between the second medial anchor device and the second distal anchor device, the second medial anchor device having one or more member portions extendable out radially therefrom and adapted to affix to a portion of the perineal membrane of the patient on a second side of the urethra, opposite the first side of the urethra, and the second distal anchor device adapted to affix to tissue away from the perineal membrane, such that the separated first and second implant devices together form a general V-shaped support configuration relative to the perineal membrane; and wherein tensioning adjustment on the first and second implant devices provides support for the urethra to restore continence.

28. The system of claim 27, wherein at least one of the first extension member and the second extension member includes a suture.

29. The system of claim 27, wherein at least one of the first extension member and the second extension member includes an elongate mesh.

30. The system of claim 27, wherein the first distal anchor device includes a first array of anchors, each of the first array of anchors having expandable barbs and being operably connected to the first extension member.

31. The system of claim 30, further including an introduction needle having a lumen extending therethrough, wherein at least the first array of anchors are adapted to traverse the lumen in a compressed state.

32. The system of claim 27, wherein the second distal anchor device includes a second array of anchors, each of the second array of anchors having expandable barbs and being operably connected to the second extension member.

33. The system of claim 27, wherein at least the first medial anchor device includes expandable fins adapted to affix the first medial anchor device to the portion of the perineal membrane.

34. The system of claim 27, wherein at least one of the first distal anchor device and the second distal anchor device is adapted to engage a target tissue site selected from the group consisting of: the obturator foramen, abdominal fascia, rectus fascia, the tendinous arch of the levator ani, the Cooper's ligament, and the pubic symphysis cartilage.

35. The system of claim 27, wherein at least one of the first medial anchor device and the first distal anchor device includes an adhesive to assist in tissue engagement.

36. The system of claim 35, wherein the adhesive is a light-activated adhesive.

* * * * *